United States Patent
Segawa

(10) Patent No.: US 11,348,234 B2
(45) Date of Patent: May 31, 2022

(54) MEDICAL IMAGE PROCESSING DEVICE, MEDICAL OBSERVATION SYSTEM, IMAGE PROCESSING METHOD, AND COMPUTER READABLE MEDIUM FOR ANALYZING BLOOD FLOW OF OBSERVATION OBJECT BEFORE AND AFTER SURGICAL RESTORATION

(71) Applicant: Sony Olympus Medical Solutions Inc., Tokyo (JP)

(72) Inventor: Kazunori Segawa, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 184 days.

(21) Appl. No.: 16/795,559

(22) Filed: Feb. 19, 2020

(65) Prior Publication Data

US 2020/0311917 A1  Oct. 1, 2020

(30) Foreign Application Priority Data

Mar. 25, 2019 (JP) .............................. JP2019-056049

(51) Int. Cl.
G06T 17/00 (2006.01)
G06T 7/00 (2017.01)
G06T 5/00 (2006.01)

(52) U.S. Cl.
CPC ............ G06T 7/0012 (2013.01); G06T 5/001 (2013.01); G06T 17/00 (2013.01); G06T 2200/04 (2013.01); G06T 2207/30104 (2013.01); G06T 2210/41 (2013.01)

(58) Field of Classification Search
CPC ....... G06T 7/0012; G06T 17/00; G06T 5/001; G06T 2200/04; G06T 2207/30104; G06T 2210/41; G06T 2207/10056; G06T 7/0016; A61B 2090/508; A61B 90/25; A61B 90/30; A61B 90/361; A61B 2505/05; A61B 5/02014; A61B 5/0071; A61B 2576/00; A61B 5/4848; A61B 5/0261; A61B 6/032; A61B 6/504; A61B 6/5217; A61B 6/5247

See application file for complete search history.

(56) References Cited

U.S. PATENT DOCUMENTS

2015/0342551 A1* 12/2015 Lavi .................... A61B 6/5235
600/431

FOREIGN PATENT DOCUMENTS

JP  2008-200274 A  9/2008

OTHER PUBLICATIONS

Joy P. Ku, Mary T. Draney, . . . "In Vivo Validation of Numerical Prediction of Blood Flow in Arterial Bypass Grafts", 2002, Annals of Biomedical Engineering, vol. 30, pp. 743-752. (Year: 2002).*

* cited by examiner

Primary Examiner — Siamak Harandi
(74) Attorney, Agent, or Firm — Xsensus LLP

(57) ABSTRACT

A medical image processing device includes circuitry configured to: analyze a blood flow flowing in an observation object based on a medical observation image obtained by capturing an image of the observation object; and generate a difference result between a simulation result of a blood flow flowing in a 3D model acquired in advance for the observation object and an analysis result of a blood flow flowing in the observation object.

13 Claims, 22 Drawing Sheets

INFRARED BLOOD FLOW IMAGE BEFORE SURGICAL RESTORATION

BLOOD FLOW ANALYSIS BEFORE SURGICAL RESTORATION

BLOOD FLOW ANALYSIS AFTER SURGICAL RESTORATION

BLOOD FLOW ANALYSIS IMAGE AFTER SURGICAL RESTORATION

3D MODEL BEFORE SURGICAL RESTORATION

SIMULATION BEFORE SURGICAL RESTORATION

3D MODEL BEFORE SURGICAL RESTORATION

3D MODEL BEFORE SURGICAL RESTORATION

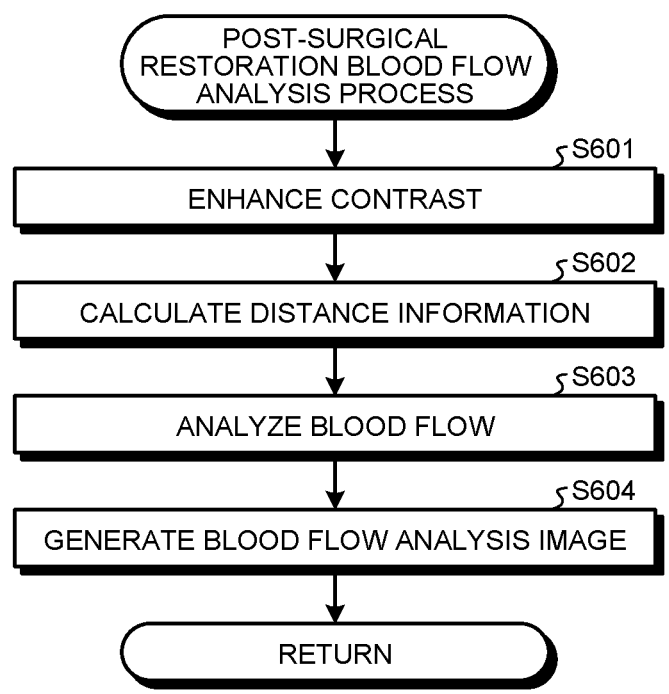

MEDICAL IMAGE PROCESSING DEVICE, MEDICAL OBSERVATION SYSTEM, IMAGE PROCESSING METHOD, AND COMPUTER READABLE MEDIUM FOR ANALYZING BLOOD FLOW OF OBSERVATION OBJECT BEFORE AND AFTER SURGICAL RESTORATION

This application claims priority from Japanese Application No. 2019-056049, filed on Mar. 25, 2019, the contents of which are incorporated by reference herein in its entirety.

BACKGROUND

The present disclosure relates to a medical image processing device, a medical observation system, an image processing method, and a computer readable recording medium.

In a medical observation system such as an X-ray diagnostic treatment apparatus, a technique of grasping an overall situation of a treatment by displaying a simulation image obtained in advance by an intravascular examination simulation apparatus and an image obtained by performing an image process on an electric signal generated by X-ray detection is known (for example, see JP 2008-200274 A). In this technique, as the simulation image, information performed based on actual patient data, a CT image, and a modality image of a magnetic resonance imaging apparatus are displayed.

SUMMARY

Incidentally, since the shape of an actual organ changes during surgery, the shape is different from the shape of the simulation image before surgery. For this reason, there are many cases in which the simulation result of the blood flow obtained using the simulation image before surgery is different from the result of the actual blood flow during surgery as in JP 2008-200274 A. Additionally, since the simulation result of the blood flow before surgery is not compared with the result of the actual blood flow after surgery in real time, there has been a desire for a technique which may be performed while reflecting a real-time comparison during surgery.

There is a need for a medical image processing device, a medical observation system, an image processing method, and a computer readable recording medium capable of comparing a simulation result of a blood flow before surgery with a result of a blood flow during surgery in real time.

According to one aspect of the present disclosure, there is provided a medical image processing device including circuitry configured to: analyze a blood flow flowing in an observation object based on a medical observation image obtained by capturing an image of the observation object; and generate a difference result between a simulation result of a blood flow flowing in a 3D model acquired in advance for the observation object and an analysis result of a blood flow flowing in the observation object.

BRIEF DESCRIPTION OF THE DRAWINGS

FIG. 30 is a flowchart illustrating an outline of a post-surgical restoration blood flow analysis process of FIG. 18.

DETAILED DESCRIPTION

Hereinafter, a mode for carrying out the present disclosure (hereinafter, referred to as "embodiments") will be described with reference to the accompanying drawings. Additionally, the present disclosure is not limited to the embodiments below. Further, the drawings referred to in the following description merely schematically illustrate shapes, sizes, and positional relationships to the extent that the contents of the present disclosure may be understood. That is, the present disclosure is not limited only to the shape, size, and positional relationship illustrated in each drawing.

First Embodiment

Schematic Configuration of Medical Observation System

Figure 1:
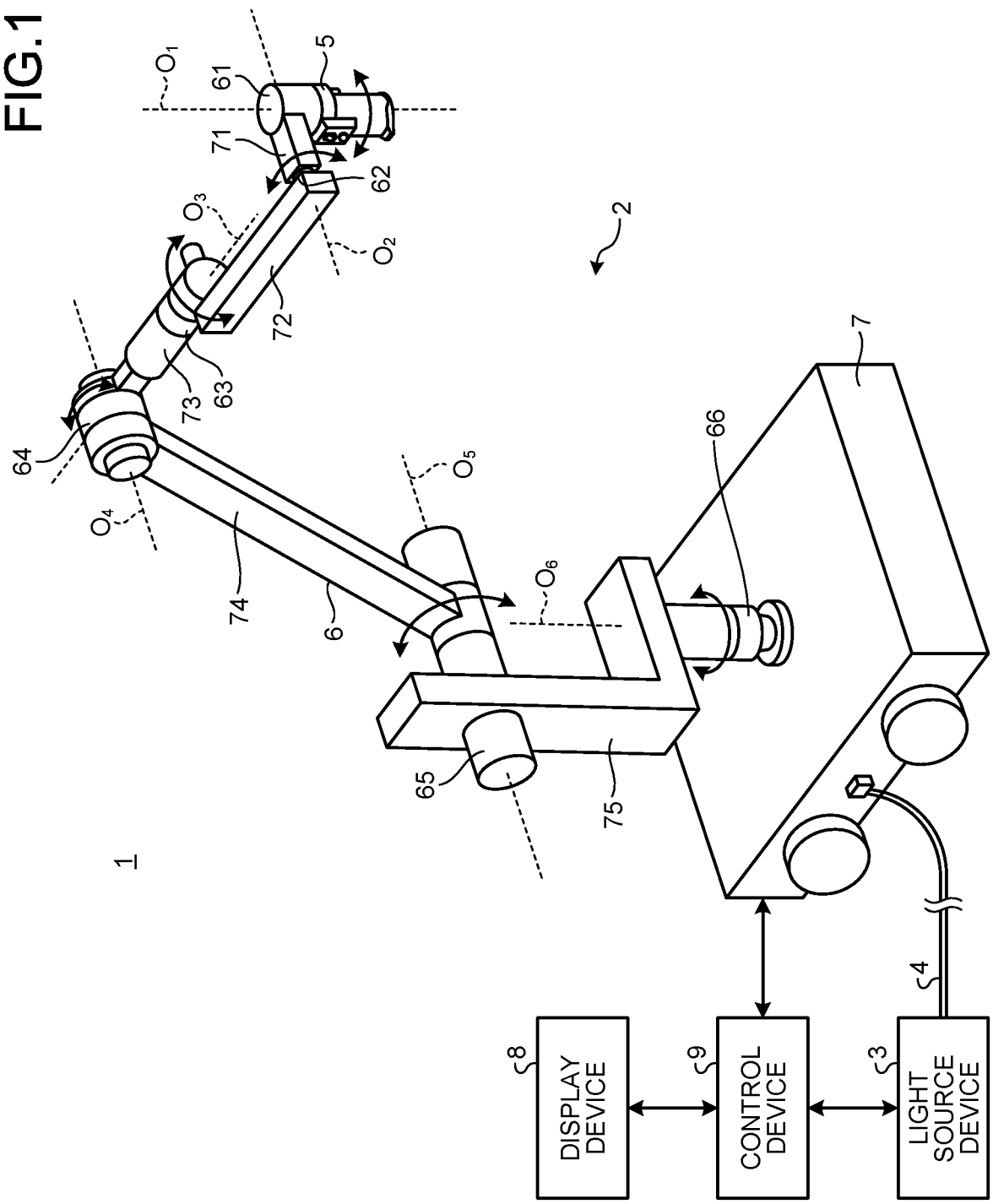
FIG. 1 is a diagram illustrating an overall configuration of a medical observation system according to a first embodiment.

FIG. 1 is a diagram illustrating an overall configuration of a medical observation system according to a first embodiment.

A medical observation system 1 illustrated in FIG. 1 includes a medical observation device 2 which has a function as a microscope magnifying and observing a minute part of an observation target, a light source device 3 which supplies illumination light to the observation device 2 through a light guide 4 formed by an optical fiber or the like, a display device 8 which displays an image captured by the observation device 2, and a control device 9 which comprehensively controls an operation of the medical observation system 1.

Schematic Configuration of Observation Device

First, a schematic configuration of the observation device 2 will be described.

The observation device 2 includes a microscope unit 5 which observes a minute part of an observation target, a support portion 6 which is connected to a base end portion of the microscope unit 5 and rotatably supports the microscope unit 5, and a base portion 7 which rotatably holds a base end portion of the support portion 6 and is movable on a floor.

Figure 2:
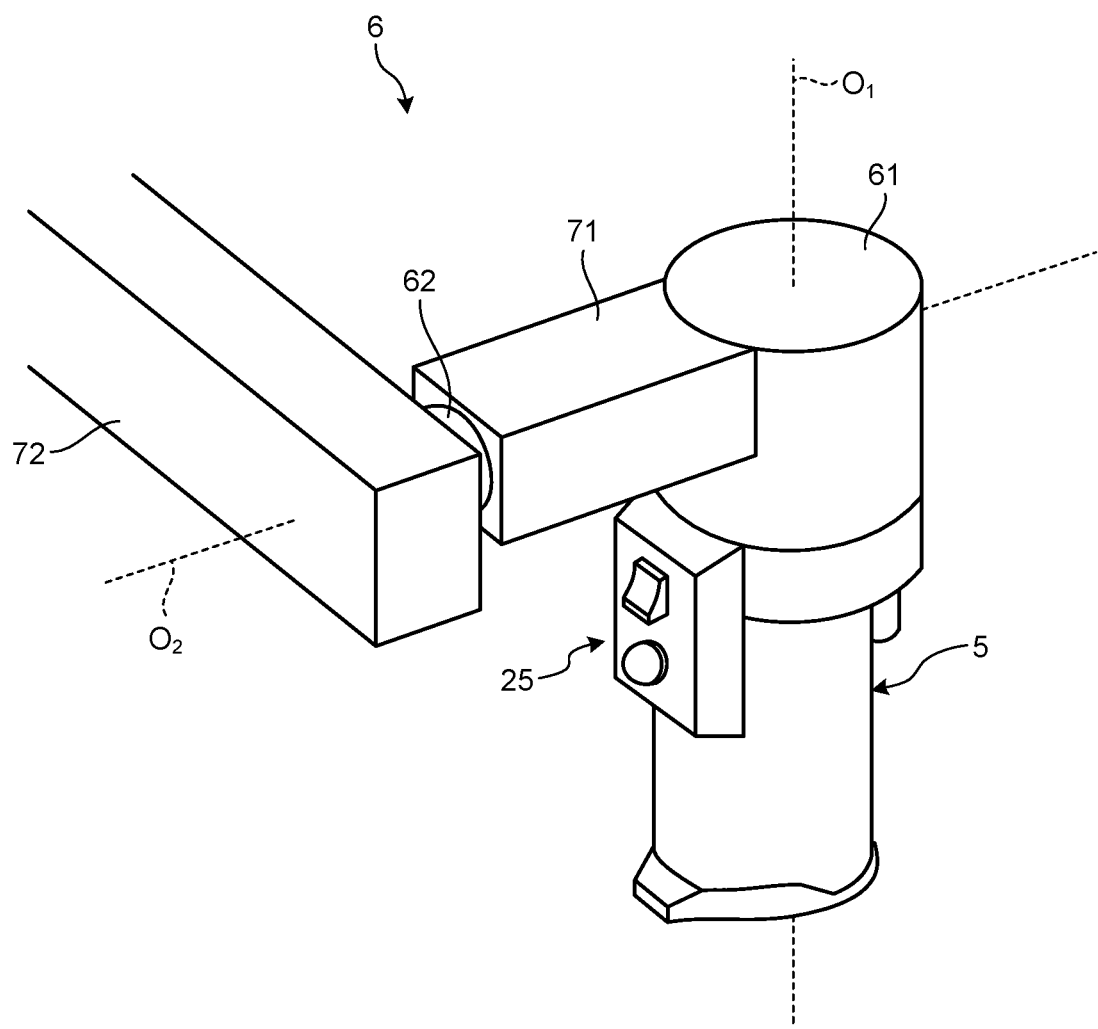
FIG. 2 is an enlarged perspective view illustrating a configuration of a microscope unit according to the first embodiment and the periphery of the microscope unit.

FIG. 2 is an enlarged perspective view illustrating a configuration of the microscope unit 5 and the periphery of the microscope unit 5.

The microscope unit 5 has a columnar appearance and includes an optical system which has a zoom function and a focus function, an imaging element (not illustrated) which receives a subject image formed by the optical system and performs photoelectric conversion so as to generate an image signal, and a light emission unit (not illustrated) which irradiates the observation target with illumination light. Further, a side surface of the microscope unit 5 is provided with various switches constituting an input unit 25 that receives an operation instruction of the observation device 2. An opening surface of a lower end portion of the microscope unit 5 is provided with a cover glass that protects the optical system or the like therein (not illustrated). A user such as an operator moves the microscope unit 5, changes the angle of the microscope unit 5, or changes the mode or zoom/focus of the observation device 2 while gripping the microscope unit 5 and operating various switches. For this reason, the user may intuitively grasp the direction of the optical axis of the optical system or the center direction of the imaging field of view of the microscope unit 5 and may easily move the microscope unit 5 to a desired position.

Additionally, the shape of the microscope unit 5 is not limited to a cylindrical shape and may be, for example, a polygonal tubular shape.

Returning to FIG. 1, a configuration of the observation device 2 will be described continuously.

A first joint portion 61, a first arm portion 71, a second joint portion 62, a second arm portion 72, a third joint portion 63, a third arm portion 73, a fourth joint portion 64, a fourth arm portion 74, a fifth joint portion 65, a fifth arm portion 75, and a sixth joint portion 66 are connected in order from the front end side (the side of the microscope unit 5) of the support portion 6.

The first joint portion 61 holds the microscope unit 5 at the front end side so as to be rotatable around a first axis $O_1$ matching the optical axis of the microscope unit 5 and is held by the first arm portion 71 at the base end side while being fixed to the front end portion of the first arm portion 71.

The second joint portion 62 holds the first arm portion 71 at the front end side so as to be rotatable around a second axis $O_2$ orthogonal to the first axis $O_1$ and is held by the second arm portion 72 at the base end side. Similarly, the third joint portion 63 to the sixth joint portion 66 respectively hold the second arm portion 72 to the fourth arm portion 74 at the front end side so as to be rotatable and are held at the base end side while being respectively fixed to the front end portions of the third arm portion 73 to the fifth arm portion 75.

The sixth joint portion 66 rotatably holds the fifth arm portion 75 at the front end side and is held at the base end side while being fixed to the base portion 7.

The second arm portion 72 to the fifth arm portion 75 are respectively rotatable around a third axis $O_3$ to a sixth axis $O_6$ as rotation axes. Each of the fourth axis $O_4$ and the fifth axis $O_5$ is parallel to the second axis $O_2$. The third axis $O_3$ is orthogonal to the fourth axis $O_4$ and the fifth axis $O_5$ is orthogonal to the sixth axis $O_6$.

The first joint portion 61 to the sixth joint portion 66 respectively include electromagnetic brakes (not illustrated) prohibiting the rotation of the front end side microscope unit 5 and the first arm portion 71 to the fifth arm portion 75 and angle sensors (not illustrated) functioning as detection units. The electromagnetic brake is released in response to a release instruction input to the input unit 25 of the microscope unit 5. The microscope unit 5 and the first arm portion 71 to the fifth arm portion 75 are respectively rotatable with respect to the first joint portion 61 to the sixth joint portion 66 when the electromagnetic brakes are released. Hereinafter, a state in which the microscope unit 5 and the first arm portion 71 to the fifth arm portion 75 are respectively rotatable with respect to the first joint portion 61 to the sixth joint portion 66 will be referred to as an all-free mode. Additionally, an air brake may be applied instead of the electromagnetic brake.

The first joint portion 61 to the sixth joint portion 66 are provided with actuators (not illustrated) respectively assisting the rotation of the microscope unit 5 and the first arm portion 71 to the fifth arm portion 75. Further, the first joint portion 61 to the sixth joint portion 66 are provided with various sensors (not illustrated) functioning as detection units respectively detecting at least a part of the position, the speed, the acceleration, the rotation angle, the rotation speed, the rotation acceleration, the torque, and the like of each joint portion.

The support portion 6 with the above-described configuration realizes a movement of the microscope unit 5 with a total of six degrees of freedom including three degrees of freedom of translation and three degrees of rotation. Additionally, the support portion 6 according to the first embodiment may not be provided with all actuators and may be modified appropriate. For example, an actuator may be provided in a part of the first arm portion 71 to the fifth arm portion 75 of the support portion 6.

The light source device 3 supplies illumination light of white light or infrared light to the observation device 2 through the light guide 4 under the control of the control device 9. The light source device 3 is configured using a discharge lamp such as a xenon lamp or a metal halide lamp, a solid light emitting element such as a Light Emitting Diode (LED) or a Laser Diode (LD), or a light emitting member such as a laser light source or a halogen lamp.

The display device 8 displays various kinds of information on the medical observation system or the display image (the video signal) generated by the control device 9. The display device 8 is configured using a liquid crystal, an organic Electro Luminescence (EL), or the like. The display device 8 displays a 2D image or a 3D image.

The control device 9 comprehensively controls each part of the medical observation system 1. The control device 9 is configured using a memory and hardware such as a general-purpose processor such as a Central Processing Unit (CPU) or a processor including various arithmetic circuits that execute a specific function such as an Application Specific Integrated Circuit (ASIC) and a Graphics Processing Unit (GPU). Further, the control device may be configured using a Field Programmable Gate Array (FPGA) (not illustrated) which is a kind of programmable integrated circuit. Additionally, in the case of using the FPGA, a memory for storing configuration data may be provided and the FPGA which is a programmable integrated circuit may be configured by the configuration data read from the memory. Additionally, a detailed configuration of the control device 9 will be described below.

Functional Configuration of Medical Observation System

Figure 3:
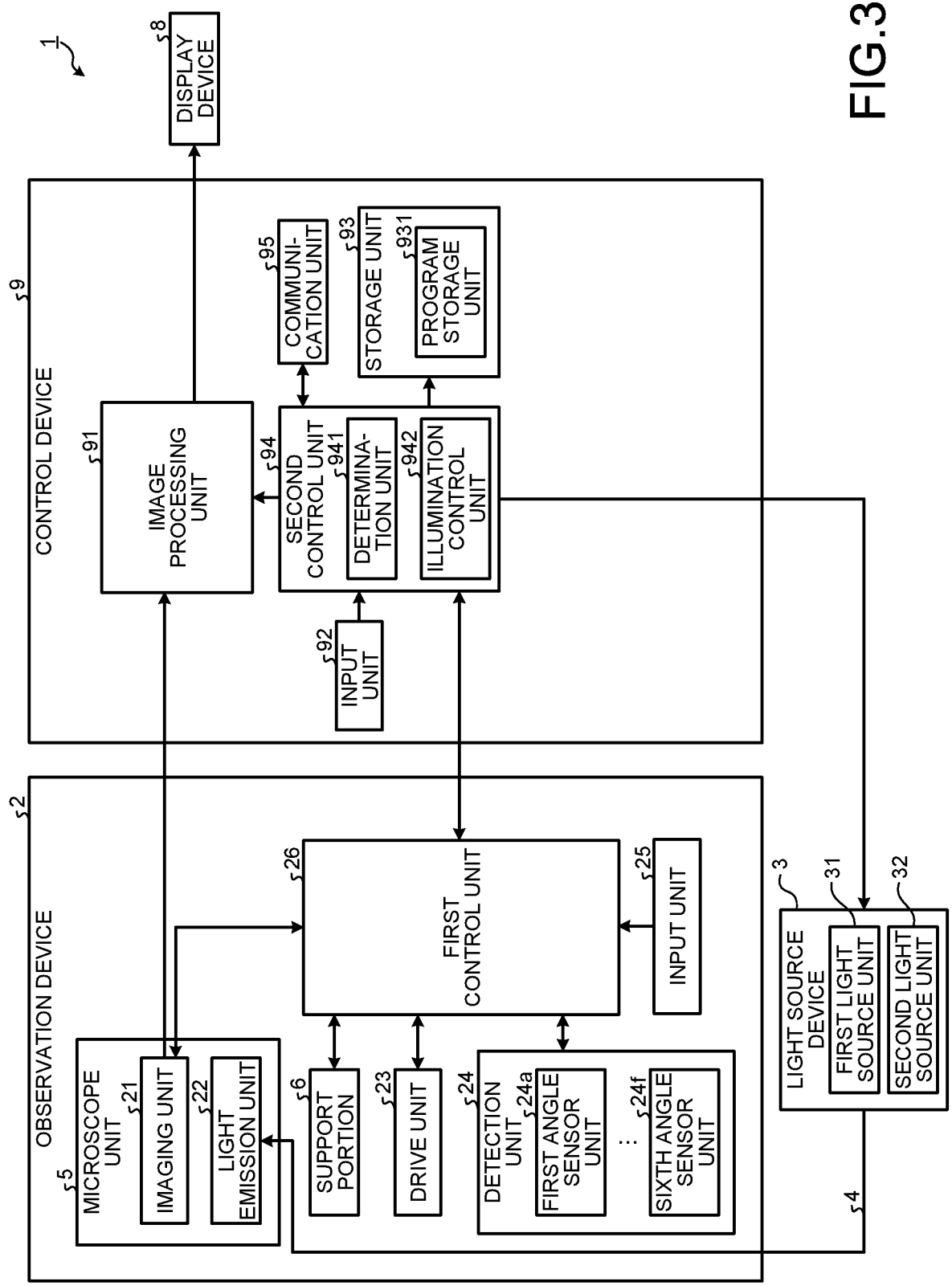
FIG. 3 is a block diagram illustrating a functional configuration of the medical observation system according to the first embodiment.

Next, a functional configuration of the medical observation system 1 will be described. FIG. 3 is a block diagram illustrating a functional configuration of the medical observation system 1.

Configuration of Observation Device

First, a functional configuration of the observation device 2 will be described.

The observation device 2 includes the microscope unit 5, the support portion 6, a drive unit 23, a detection unit 24, an input unit 25, and a first control unit 26.

The microscope unit 5 includes an imaging unit 21 which generates an image signal by magnifying and capturing an image of an observation target which is an observation object and a light emission unit 22 which emits illumination light supplied from the light source device 3 toward the observation target.

The imaging unit 21 includes a pair of left and right optical systems having a zoom and focus function and two imaging elements for 3D image data having parallax obtained by receiving an image of an observation target formed by the pair of left and right optical systems and performing photoelectric conversion. The imaging element is configured using a Charge Coupled Device (CCD) or a Complementary Metal Oxide Semiconductor (CMOS). The imaging signal generated by the imaging unit 21 is transmitted to the control device 9 through a transmission cable. Additionally, the imaging signal may be transmitted to the control device 9 through an optical signal by performing an E/O conversion on the imaging signal generated by the imaging unit 21. Additionally, the imaging unit 21 may have, for example, a resolution of, for example, 2 megapixels (for example, a so-called 2K resolution of 1920×1080 pixels) or more, desirably a resolution of 8 megapixels (for example, a so-called 4K resolution of 3840×2160 pixels) or more, and more desirably a resolution of 32 megapixels (for example, a so-called 8K resolution of 7680×4320 pixels) or more.

The light emission unit 22 includes an illumination optical system configured using one or a plurality of lenses. The light emission unit 22 emits illumination light of white light or infrared light supplied from the light source device 3 through the light guide 4 in the same direction as the imaging direction of the imaging unit 21. Additionally, the light emission unit 22 may omit light transmission such as a light guide by providing a Light Emitting Diode (LED) or a laser light source in the microscope unit 5.

The support portion 6 rotatably supports the microscope unit 5 as in FIGS. 1 and 2. The support portion 6 realizes a movement of the microscope unit 5 with a total of six degrees of freedom including three degrees of freedom of translation and three degrees of rotation.

The drive unit 23 includes electromagnetic brakes and actuators respectively provided in the first joint portion 61 to the sixth joint portion 66. The electromagnetic brake is released in accordance with a release instruction input to the input unit 25 during the operation in an all-free mode. The actuator is operated in response to a control signal transmitted from the control device 9 to be described later in response to a state detection result of the detection unit 24.

The detection unit 24 sequentially detects the state information of the observation device 2. The state information of the observation device 2 includes information on the position, focus, and zoom of the imaging unit 21, information on at least one of the position, speed, acceleration, rotation angle, rotation speed, rotation acceleration, and torque of the first joint portion 61 to the sixth joint portion 66, information on at least a part of the position, speed, and acceleration of the first arm portion 71 to the fifth arm portion 75, and information on the operation in the motorized view mode (the pivot operation mode or XY operation mode) and the operation in the all-free mode. The detection unit 24 includes various sensors for detecting these kinds of information. Specifically, the detection unit 24 includes a first angle sensor unit 24a to a sixth angle sensor unit 24f which respectively detect the angles of the first arm portion 71 to the fifth arm portion 75 (the first axis $O_1$ to the sixth axis $O_6$) with respect to the reference direction. Here, the reference direction is the gravity direction (the vertical direction) when the observation device 2 (the first arm portion 71 to the fifth arm portion 75) is installed on a floor. That is, in the first embodiment, a description will be made such that the reference direction is 0°. Of course, the reference direction changes depending on the installation position of the observation device 2 (the first arm portion 71 to the fifth arm portion 75). For example, when the installation position of the observation device 2 (the first arm portion 71 to the fifth arm portion 75) is a ceiling, the reference direction is different by 180° as compared with the floor installation case. Further, when the installation position of the observation device 2 (the first arm portion 71 to the fifth arm portion 75) is a wall (to be fixed to a vertical wall), the reference direction is different by 90° as compared with the floor installation case. Additionally, when the direction of the first axis $O_1$ detected by the first angle sensor unit 24a is the same as the imaging direction of the imaging unit 21, the first angle sensor unit 24a may be omitted.

Here, the motorized view mode (the XY operation mode) is an operation mode in which a part of axes of a plurality of joint portions constituting the support portion 6 is fixed and the imaging field of view of the imaging unit 21 is changeable up, down, left, and right by the movement of another axis. Specifically, the motorized view mode (the XY operation mode) is an operation mode in which the imaging field of view of the imaging unit 21 is changeable up, down, left, and right by electrically operating only the second axis $O_2$ and the third axis $O_3$ while the fourth axis $O_4$ to the sixth axis $O_6$ are fixed.

Further, the pivot operation mode is a turning operation in which the microscope unit 5 moves by the movement of the support portion 6 on a conical surface having one point as a vertex while the microscope unit is fixed at one point in the center direction of the imaging field of view of the imaging unit 21 and is also called a point lock operation. The turning axis of the pivot operation mode is the center axis in the height direction of the cone. In the pivot operation mode, a distance between the fixed point and the imaging unit 21 is maintained uniformly. During surgery, for example, a surgical site is selected as the fixed point. According to such a pivot operation mode, since it is possible to observe the surgical site at the same distance from different angles, the user may more accurately grasp the surgical site.

The input unit 25 receives an operation instruction to the imaging unit 21 and the drive unit 23. The input unit 25 includes an arm operation switch which releases the electromagnetic brake of the drive unit 23 and receives an instruction of an all-free mode, a focus/zoom switch which receives an input of a focus/zoom operation in the imaging unit 21, a motorized view mode switch which receives an input of an instruction of a motorized view mode, and a power assist switch which receives an input of an instruction of a power assist mode. Various switches or buttons constituting the input unit 25 are provided on the side surface of the microscope unit 5 as illustrated in FIG. 2. Additionally, a part of various switches or buttons constituting the input unit 25 is described in FIG. 2. Additionally, in the first embodiment, the input unit 25 functions as a first input unit.

The first control unit 26 controls the operations of the imaging unit 21 and the drive unit 23 in response to an operation instruction to the input unit 25 or an operation instruction from the control device 9 to be described later. Further, the first control unit 26 comprehensively controls the observation device 2 in cooperation with a second control unit 94 of the control device 9 to be described later. The first control unit 26 is configured using a memory and a processor having hardware such as a CPU and an ASIC.

Configuration of Light Source Device

Next, a configuration of the light source device 3 will be described.

The light source device 3 includes a first light source unit 31 and a second light source unit 32.

The first light source unit 31 supplies white light to the light emission unit 22 of the observation device 2 through the light guide 4 under the control of the control device 9. The first light source unit 31 is configured using a white Light Emitting Diode (LED) or a xenon lamp.

The second light source unit 32 supplies infrared light for exciting a fluorescent substance to the light emission unit 22 of the observation device 2 through the light guide 4. The second light source unit 32 supplies infrared light (a wavelength band of 700 to 1000 nm) for exciting a fluorescent substance under the control of the control device 9. The second light source unit 32 is configured using a semiconductor laser device capable of irradiating infrared light (700 to 1000 nm) used for Indocyanine Green (ICG) observation, a filter transmitting only a predetermined wavelength band, and the like. Additionally, in the description below, a description will be made as the infrared light, but the present disclosure is not limited thereto. For example, light used for Photo Dynamic Diagnosis (PDD) observation (wavelength band of around 405 nm) in which a photosensitizer such as a hematoporphyrin derivative is preliminarily accumulated in tumor tissue to observe fluorescence and light (wavelength band of 390 to 470 nm+wavelength band of 540 to 560 nm) used for Auto Fluorescence Imaging (AFI) observation for observing self-emission from a fluorescent substance such as collagen may be used.

Configuration of Control Device

Next, a functional configuration of the control device 9 will be described.

The control device 9 includes an image processing unit 91, an input unit 92, a storage unit 93, a second control unit 94, and a communication unit 95.

The image processing unit 91 performs E/O conversion on the imaging signal of the optical signal transmitted from the observation device 2 and then performs a predetermined image process thereon so as to generate a display image (a video signal) displayed by the display device 8. Here, as the image process, various image processes such as color correction, color enhancement, contour enhancement, and mask processing may be exemplified. The image processing unit 91 is configured using a memory and a processor including hardware such as a GPU or FPGA. Additionally, a detailed configuration of the image processing unit 91 will be described later.

The input unit 92 is realized using a user interface such as a keyboard, a mouse, and a touch panel and receives various kinds of information.

The storage unit 93 is configured using a semiconductor memory such as a flash memory or a Dynamic Random Access Memory (DRAM) and includes a program storage unit 931 which temporarily stores various programs executed by the medical observation system 1 or data to be processed.

The second control unit 94 comprehensively controls each part of the medical observation system 1. The second control unit 94 is realized using a general-purpose processor such as a CPU having an internal memory (not illustrated) storing a program or a dedicated processor such as an arithmetic circuit that executes a specific function such as an ASIC. Further, the second control unit may be configured using an FPGA which is a kind of programmable integrated circuit. Additionally, in the case of using the FPGA, a memory that stores configuration data may be provided and the FPGA that is a programmable integrated circuit may be configured by the configuration data read from the memory. The second control unit 94 includes a determination unit 941 which determines the operation content of the input unit 92 and an illumination control unit 942 which switches the illumination light to be irradiated by the light source device 3 based on the determination result of the determination unit 941.

The communication unit 95 may communicate with the outside and acquire CT image data or MRI image data from an external server under the control of the second control unit 94. Specifically, the communication unit 95 acquires a 3D model of an observation object including an organ of a subject to be treated and generated by a CT device or MRI device in advance and a simulation result of a blood flow flowing in the 3D model from the outside.

Detailed Configuration of Image Processing Device

Next, a detailed configuration of the image processing unit 91 will be described.

Figure 4:
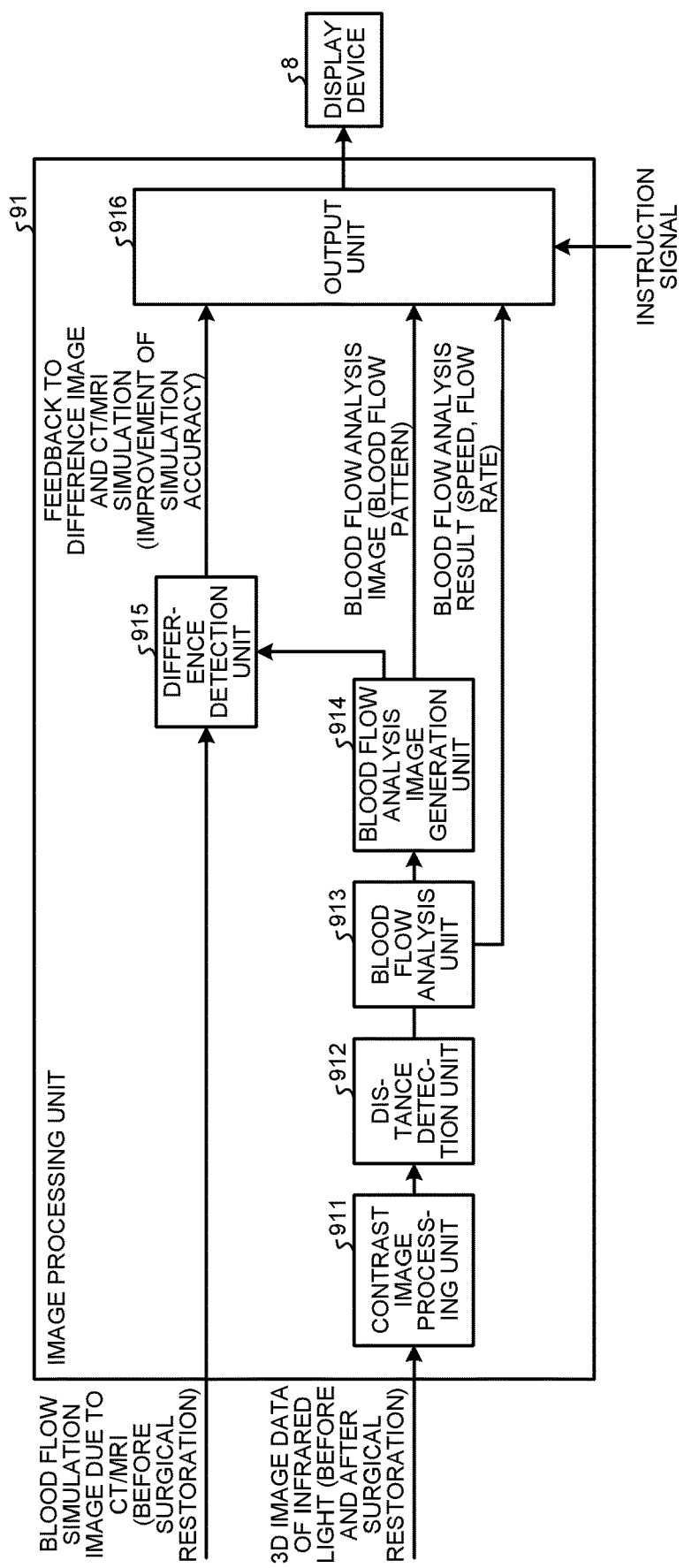
FIG. 4 is a block diagram illustrating a functional configuration representing a detailed configuration of an image processing unit according to the first embodiment.

FIG. 4 is a block diagram illustrating a functional configuration indicating a detailed configuration of the image processing unit 91.

The image processing unit 91 illustrated in FIG. 4 includes a contrast image processing unit 911, a distance detection unit 912, a blood flow analysis unit 913, a blood flow analysis image generation unit 914, a difference detection unit 915, and an output unit 916. Additionally, in the first embodiment, the image processing unit 91 functions as a medical image processing device.

The contrast image processing unit 911 performs an image process of enhancing contrast on two 3D image data generated by the irradiation of the infrared light before and after surgical restoration of the observation object and input from the observation device 2 and outputs a result to the distance detection unit 912.

The distance detection unit 912 detects distance information including a length in the vertical direction, a length in the horizontal direction, and a length in the depth direction of the observation object based on the 3D image data input from the contrast image processing unit 911 and outputs the distance information to the blood flow analysis unit 913. Specifically, the distance detection unit 912 detects distance information of the observation object (the organ) by using a known stereo method. Additionally, the distance detection unit 912 may detect shape or position of the observation object (the organ).

The blood flow analysis unit 913 analyzes a blood flow flowing in the observation object based on the medical observation image obtained by capturing an image of the observation object. Specifically, the blood flow analysis unit 913 analyzes the blood flow flowing in each observation object (the organ) before and after surgical restoration based on two 3D image data generated by the irradiation of the infrared light before and after surgical restoration of the observation object based on the distance information calculated by the distance detection unit 912 and outputs the analysis result to the blood flow analysis image generation unit 914. For example, the blood flow analysis unit 913 detects a thickness of a blood vessel of the organ which is the observation object based on the distance information calculated by the distance detection unit 912 and analyzes the flow of the blood flow, the flow speed of the blood flow, the flow rate of the blood flow, and the flow pattern of the blood flow based on the detected thickness of the blood vessel and the known fluid dynamics of the liquid.

The blood flow analysis image generation unit 914 generates the blood flow analysis image based on the blood flow analysis result analyzed by the blood flow analysis unit and outputs the blood flow analysis image to the difference detection unit 915. Specifically, the analysis result analyzed by the blood flow analysis unit 913 is combined with the 3D model acquired in advance through the communication unit 95 or the superimposed image is generated as the blood flow analysis image.

The difference detection unit 915 generates a difference result between the simulation result of the blood flow flowing in the 3D model of the observation object acquired in advance through the communication unit 95 and the analysis result of the blood flow flowing in the observation object analyzed by the blood flow analysis unit 913 and outputs the generated difference result to the output unit 916. Further, the difference detection unit 915 may generate a difference result between the simulation image of the blood flow flowing in the 3D model of the observation object acquired in advance through the communication unit 95 and each blood flow analysis image before and after surgical restoration generated by the blood flow analysis image generation unit 914 and output the difference result to the output unit 916.

The output unit 916 selects any one or more of the difference result detected by the difference detection unit 915, each blood flow analysis result before and after surgical restoration, each blood flow analysis image before and after surgical restoration, and the simulation image based on the instruction signal input from the input unit 92 or the input unit 25 and outputs the selected one to the display device 8. Additionally, the output unit 916 may select and display any one or more of the difference result detected by the difference detection unit 915, each blood flow analysis result before and after surgical restoration, each blood flow analysis image before and after surgical restoration, and the simulation image on the display device 8 and transmit at least one or more of each blood flow analysis result before and after surgical restoration, each blood flow analysis image before and after surgical restoration, and the simulation image to an external server, for example, a server including an external Hard Disk Drive (HDD) or the like, a terminal device including a memory card or the like, or a processing device.

Process of Image Processing Unit

Figure 5:
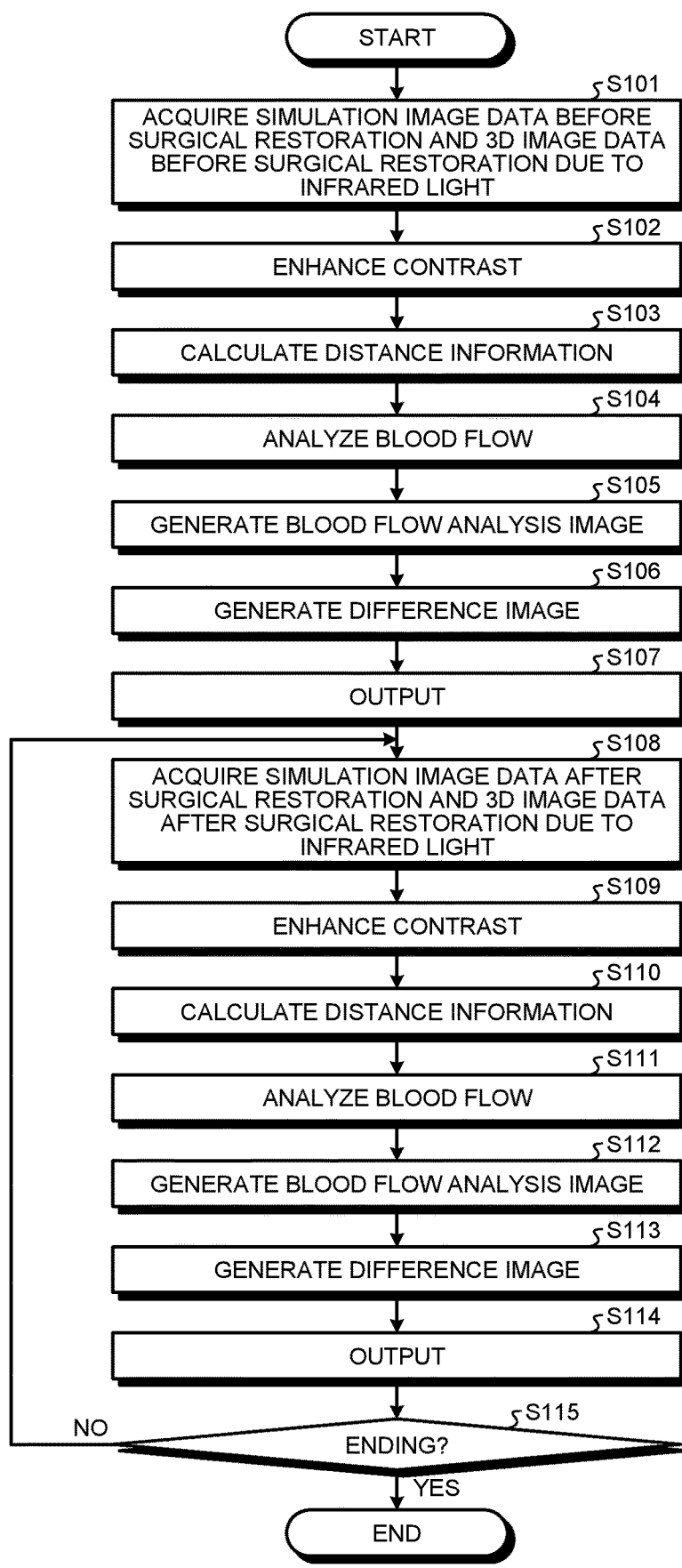
FIG. 5 is a flowchart illustrating an outline of a process performed by the image processing unit according to the first embodiment.
Figure 6:
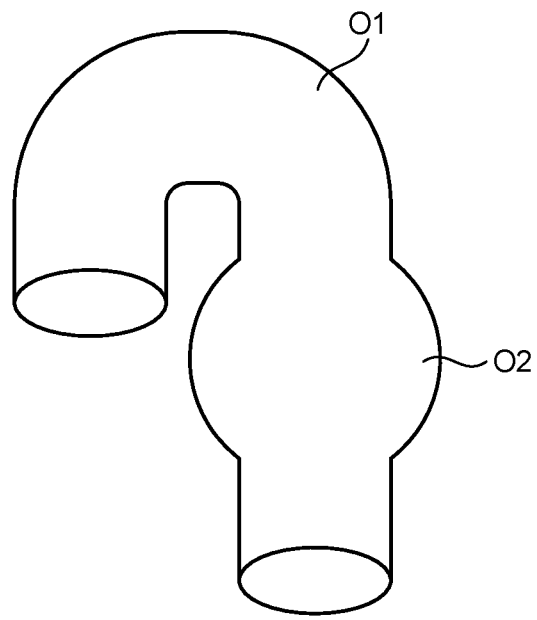
FIG. 6 is a diagram schematically illustrating a 3D model of an aortic aneurysm before surgical restoration according to the first embodiment.
Figure 7:
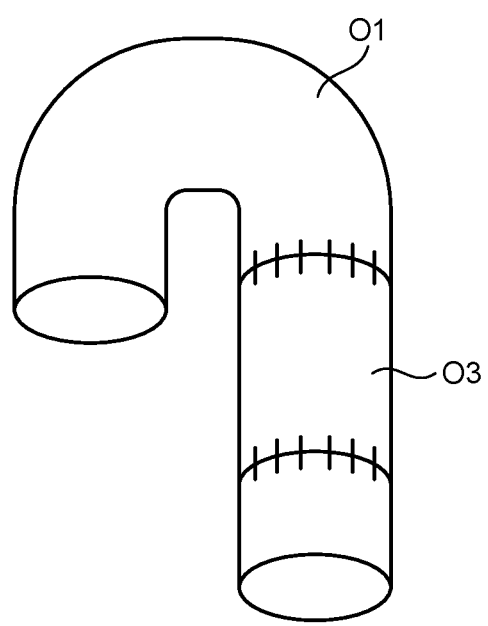
FIG. 7 is a diagram schematically illustrating a 3D model of an aortic aneurysm after surgical restoration.

Next, a process executed by the image processing unit 91 will be described. FIG. 5 is a flowchart illustrating an outline of a process executed by the image processing unit 91. Additionally, in the description below, a process for simulating a blood flow of an aortic aneurysm as an observation object will be described. FIG. 6 is a diagram schematically illustrating a 3D model of the aortic aneurysm before surgical restoration. FIG. 7 is a diagram schematically illustrating a 3D model of the aortic aneurysm after surgical restoration. In FIGS. 6 and 7, a simulation of blood flow when replacing an aortic aneurysm O2 in an aorta O1 with an artificial blood vessel O3 will be described.

As illustrated in FIG. 5, the image processing unit 91 first acquires the 3D image data before surgical restoration due to infrared light from the observation device 2 and the blood flow simulation image data through the communication unit 95 (Step S101). Specifically, the image processing unit 91 acquires simulation image data of the blood flow flowing in a subject, for example, an organ before and after surgery generated by a CT or MRI device from an external server (not illustrated) through the communication unit 95. Further, the image processing unit 91 acquires 3D image data generated using the imaging unit 21 by capturing an image of the organ (the aorta O1) before surgical restoration (surgery) injected with ICG when the observation device 2 irradiates the infrared light.

Subsequently, the contrast image processing unit 911 performs an image process of enhancing contrast on the 3D image data and outputs the data to the distance detection unit 912 (Step S102). For example, the contrast image processing unit 911 performs a conversion process of converting a density value using a known contrast conversion function and a histogram, a density conversion process using a look-up table, and the like.

Then, the distance detection unit 912 calculates distance information including a length in the vertical direction, a length in the horizontal direction, and a length in the depth direction based on the 3D image data which is input from the contrast image processing unit 911 and of which contrast is enhanced (Step S103). Additionally, the distance detection unit 912 may detect the position of the observation object, for example, the major aorta O1 or aortic aneurysm O2 based on the 3D image data which is input from the contrast image processing unit 911 and of which contrast is enhanced.

Then, the blood flow analysis unit 913 analyzes the blood flow flowing in the organ based on the distance information calculated by the distance detection unit 912 (Step S104). Specifically, the blood flow analysis unit 913 analyzes the speed, diversion, and pattern of the blood flow flowing in the aorta O1 and the aortic aneurysm O2 before surgical restoration based on the simulation image based on the simulation image data acquired by the communication unit 95 from the outside and the distance information detected by the distance detection unit 912.

Figure 8:
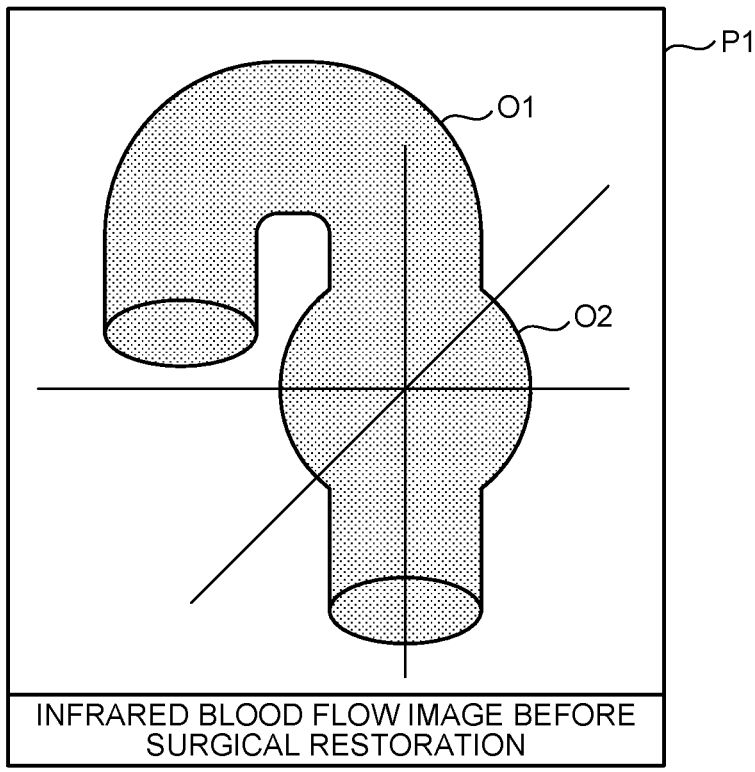
FIG. 8 illustrates an example of an infrared blood flow image before surgical restoration.
Figure 9:
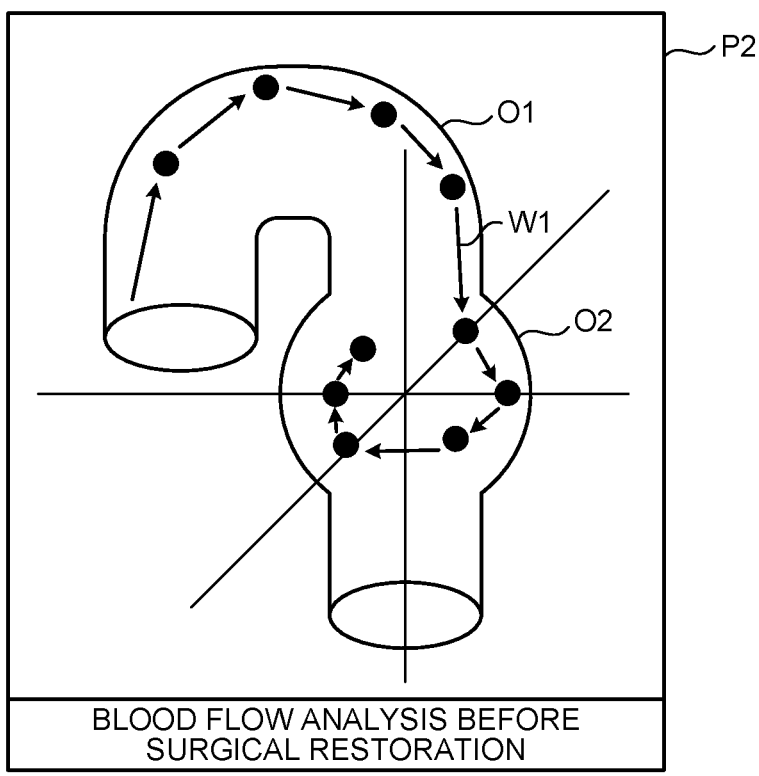
FIG. 9 illustrates an example of an infrared blood flow analysis image before surgical restoration.
Figure 10:
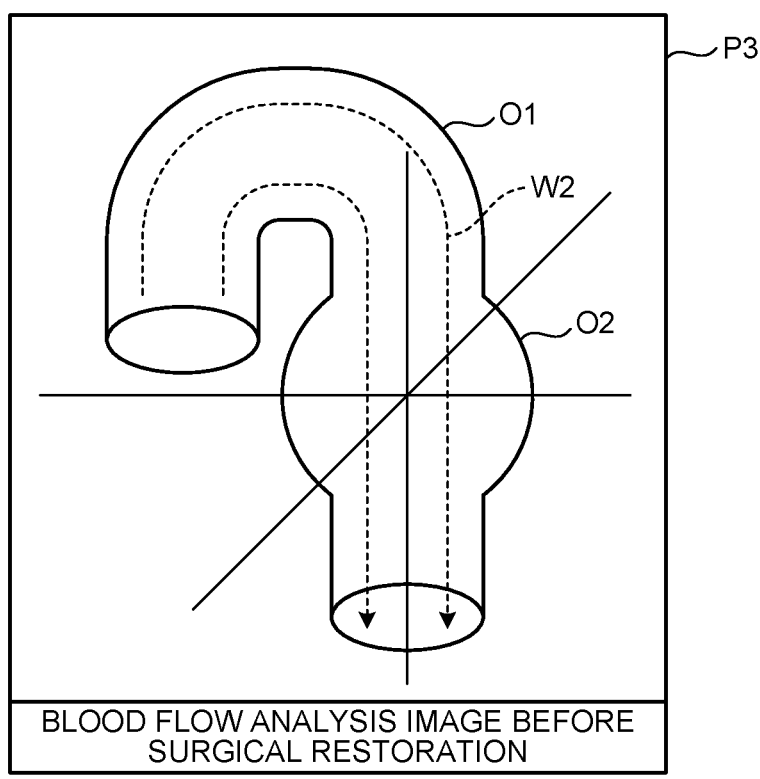
FIG. 10 illustrates another example of a blood flow analysis image before surgical restoration.

Subsequently, the blood flow analysis image generation unit 914 generates the blood flow analysis image based on the blood flow analysis result analyzed by the blood flow analysis unit 913 (Step S105). Specifically, the blood flow analysis image generation unit 914 generates blood flow analysis images of the speed, diversion, and pattern of the blood flow in the aorta O1 and the aortic aneurysm O2 of the simulation image before surgical restoration based on the blood flow analysis result analyzed by the blood flow analysis unit 913. FIG. 8 illustrates an example of the infrared blood flow image before surgical restoration. FIG. 9 illustrates an example of the infrared blood flow analysis image before surgical restoration. FIG. 10 illustrates another example of the blood flow analysis image before surgical restoration. As illustrated in FIGS. 8 to 10, the blood flow analysis image generation unit 914 generates an infrared blood flow image P1, a blood flow analysis image P2, and a blood flow analysis image P3 based on the blood flow analysis result generated by the blood flow analysis unit 913. The blood flow analysis image P2 includes a blood flow speed and a blood flow pattern W1. Further, the blood flow analysis image P3 includes a blood flow rate W2.

Figure 11:
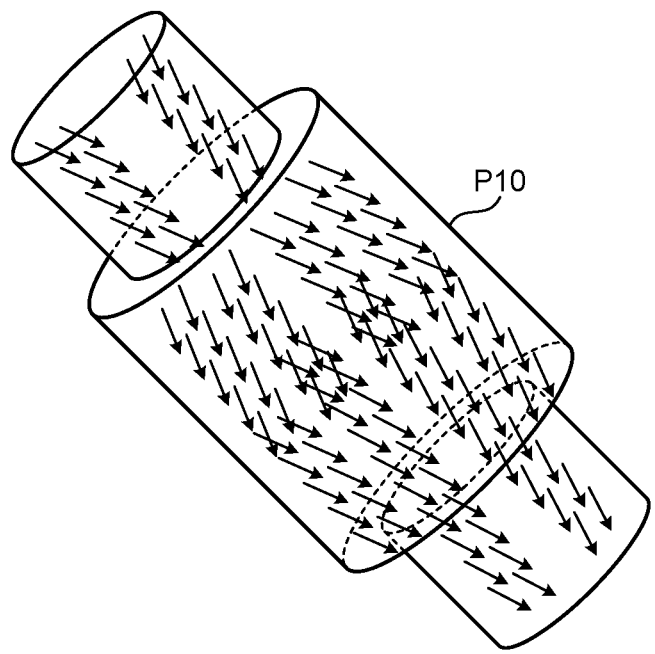
FIG. 11 is a diagram schematically illustrates a blood flow flowing in a simulation image before surgical restoration.
Figure 12:
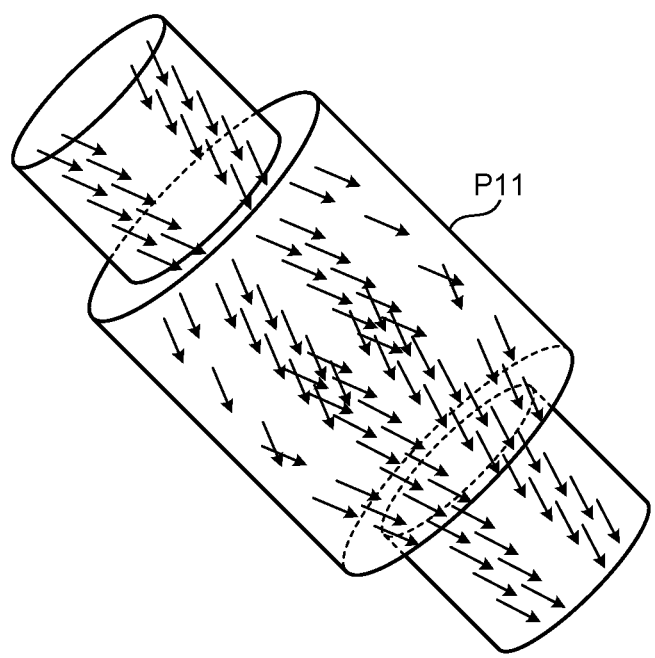
FIG. 12 is a diagram schematically illustrating a blood flow analysis image before surgical restoration generated by a blood flow analysis image generation unit according to the first embodiment.
Figure 13:
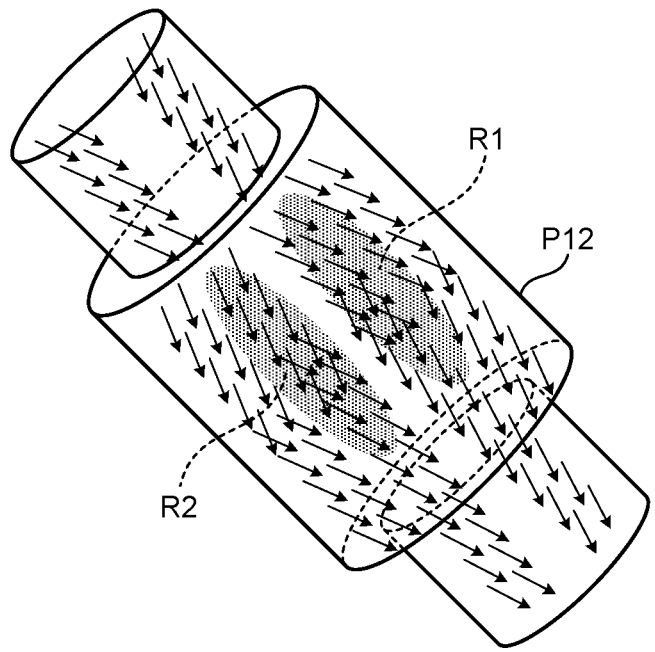
FIG. 13 is a diagram schematically illustrating a difference image before surgical restoration detected by a difference detection unit according to the first embodiment.

Then, the difference detection unit 915 generates a difference image indicating a difference result between a simulation image obtained by simulating the blood flow flowing in the 3D model acquired through the communication unit 95 and a blood flow analysis image generated by the blood flow analysis image generation unit 914 (Step S106). FIG. 11 is a diagram schematically illustrating a blood flow flowing in the simulation image before surgical restoration. FIG. 12 is a diagram schematically illustrating a blood flow image generated by the blood flow analysis image generation unit 914 before surgical restoration. FIG. 13 is a diagram schematically illustrating a difference image detected by the difference detection unit 915. As illustrated in FIGS. 11 to 13, the difference detection unit 915 detects regions R1 and R2 having a difference in the flow of the blood flow (indicated by a plurality of arrows in FIGS. 11 to 13) flowing in each of a simulation image P10 before surgical restoration and a blood flow analysis image P11 before surgical restoration and generates a difference image P12 before surgical restoration in which the regions R1 and R2 may be identified, for example, highlighted in red.

Subsequently, the output unit 916 outputs any one or more of the simulation image, the difference image P12 detected by the difference detection unit 915, the blood flow analysis image (the blood flow pattern), and the blood flow analysis result to the display device 8 based on the instruction signal input from the input unit 92 through the second control unit 94 (Step S107). Accordingly, the user may intuitively grasp a difference between the blood flow of the simulation image before surgical restoration of the observation object and the actual blood flow due to infrared light in real time. Additionally, the output unit 916 may output the simulation image, the difference image P12 detected by the difference detection unit 915, the blood flow analysis image (the blood flow pattern), and the blood flow analysis result to the display device 8. Accordingly, the operator may grasp the state of the aortic aneurysm O2 before surgical restoration while comparing the simulation image, the blood flow analysis image P2, and the difference image P12. Further, the output unit 916 may output the simulation image, the difference image P12 detected by the difference detection unit 915, the blood flow analysis image (the blood flow pattern), and the blood flow analysis result to a storage device provided in an external server or the like. Accordingly, the simulation device which generates the simulation image may improve the accuracy of the simulation of the blood flow of the 3D model. Further, since the operator may perform medical verification after surgery, for example, a comparison of the result of each surgical restoration by checking the result of the storage device, this may be used for feedback to future procedures and surgery.

Subsequently, the image processing unit 91 acquires the 3D image data after surgical restoration due to infrared light from the observation device 2 and the blood flow simulation image data after surgical restoration through the communication unit 95 (Step S108).

Then, the contrast image processing unit 911 performs an image process of enhancing contrast on the 3D image data after surgical restoration and outputs the data to the distance detection unit 912 (Step S109).

Subsequently, the distance detection unit 912 calculates the distance information including a length in the vertical direction, a length in the horizontal direction, and a length in the depth direction of the observation object based on the 3D image data after surgical restoration which is input from the contrast image processing unit 911 and of which contrast is enhanced (Step S110).

Then, the blood flow analysis unit 913 analyzes the blood flow flowing in the organ based on the distance information detected by the distance detection unit 912 (Step S111). Specifically, the blood flow analysis unit 913 analyzes the speed, diversion, and pattern of the blood flow flowing in the aorta O1 and the artificial blood vessel O3 of the simulation image after surgical restoration based on the distance information detected by the distance detection unit 912 and the simulation image after surgical restoration based on the simulation image after surgical restoration data acquired by the communication unit 95 from the outside.

Figure 14:
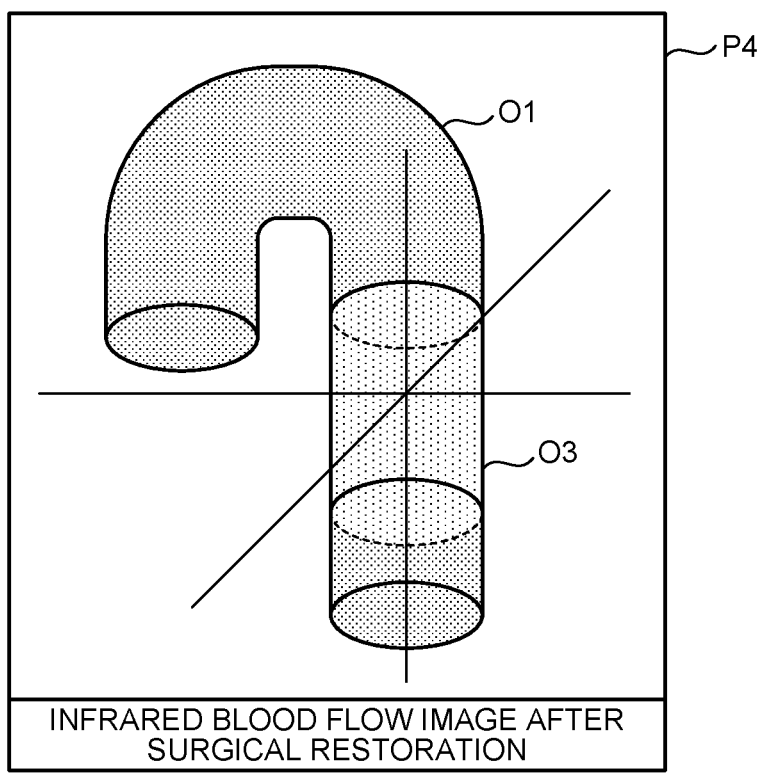
FIG. 14 illustrates an example of an infrared blood flow image after surgical restoration.
Figure 15:
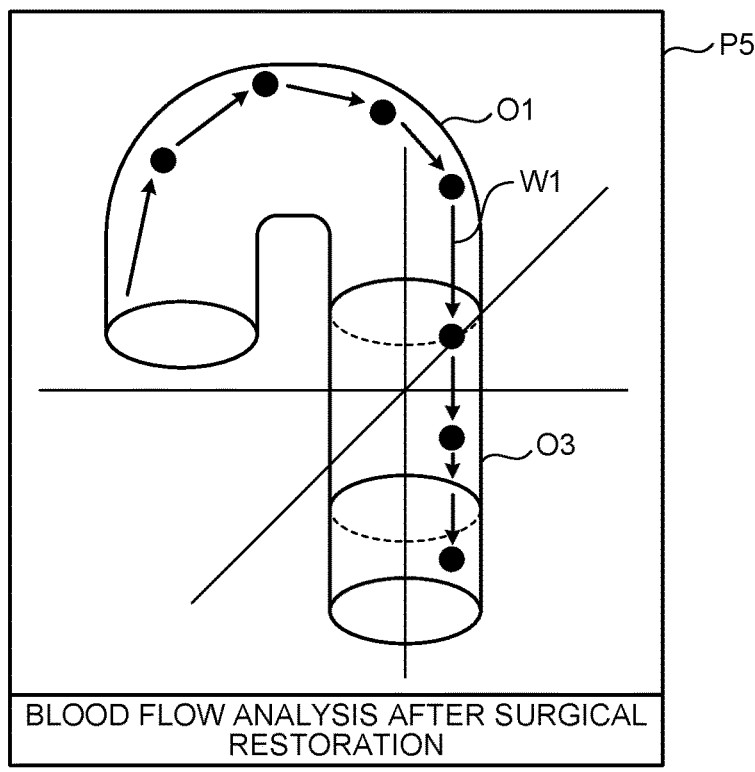
FIG. 15 illustrates an example of an infrared blood flow analysis image after surgical restoration.
Figure 16:
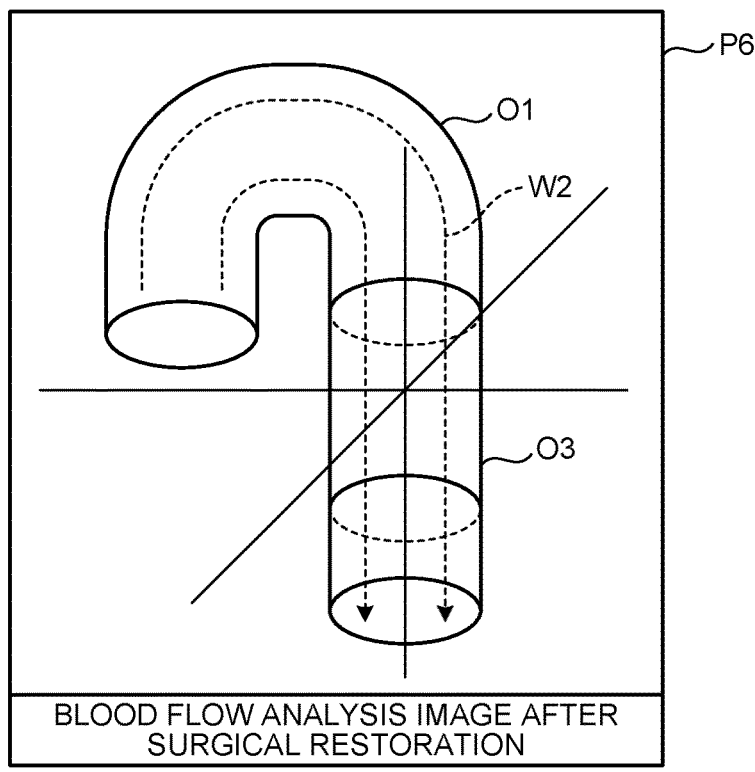
FIG. 16 illustrates another example of a blood flow analysis image after surgical restoration.

Subsequently, the blood flow analysis image generation unit 914 generates the blood flow analysis image based on the blood flow analysis result analyzed by the blood flow analysis unit 913 (Step S112). Specifically, the blood flow analysis image generation unit 914 generates the blood flow analysis images of the speed, diversion, and pattern of the blood flow flowing in the aorta O1 and the artificial blood vessel O3 in the simulation image after surgical restoration based on the blood flow analysis result analyzed by the blood flow analysis unit 913. FIG. 14 illustrates an example of the infrared blood flow image after surgical restoration. FIG. 15 illustrates an example of the infrared blood flow analysis image after surgical restoration. FIG. 16 illustrates another example of the blood flow analysis image after surgical restoration. As illustrated in FIGS. 14 to 16, the blood flow analysis image generation unit 914 generates an infrared blood flow image P4 after surgical restoration, a blood flow analysis image P5 after surgical restoration, and a blood flow analysis image P6 after surgical restoration based on the blood flow analysis result analyzed by the blood flow analysis unit 913. The blood flow analysis image P5 after surgical restoration includes the blood flow speed and the blood flow pattern W1. Further, the blood flow analysis image P6 after surgical restoration includes a blood flow rate W2.

Then, the difference detection unit 915 generates a difference image indicating a difference result between a simulation image obtained by simulating the blood flow flowing in the 3D model acquired through the communication unit 95 and a blood flow analysis image generated by the blood flow analysis image generation unit 914 (Step S113). Specifically, the difference detection unit 915 detects a flow region having a difference in the flow of the blood flow flowing in the simulation image after surgical restoration and the blood flow analysis image after surgical restoration and generates a difference image in which this flow region may be identified. For example, the difference detection unit 915 detects a region having a difference in the flow of the blood flow flowing in each of the simulation image after surgical restoration and the blood flow analysis image after surgical restoration according to the same method as the regions R1 and R2 having a difference in the flow of the blood flow flowing in each of the simulation image P10 before surgical restoration illustrated in FIGS. 11 to 13 and the blood flow analysis image P11 before surgical restoration and generates a difference image in which this region may be identified.

Subsequently, the output unit 916 outputs any one or more of the simulation image, the difference image after surgical restoration detected by the difference detection unit 915, the blood flow analysis image (the blood flow pattern) after surgical restoration, and the blood flow analysis result after surgical restoration to the display device 8 based on the instruction signal input from the input unit 92 through the second control unit 94 (Step S114). Accordingly, the user may intuitively grasp a difference between the blood flow of the simulation image after surgical restoration of the observation object and the actual blood flow due to infrared light in real time. Additionally, the output unit 916 may output the simulation image, the difference image after surgical restoration detected by the difference detection unit 915, the blood flow analysis image (the blood flow pattern) after surgical restoration, and the blood flow analysis result after surgical restoration to the display device 8. Accordingly, the operator may grasp the state of the aorta O1 and the artificial blood vessel O3 after surgical restoration while comparing the simulation image, the blood flow analysis image P2, and the difference image.

Then, when an instruction signal of instructing the ending is input from the input unit 92 through the second control unit 94 (Step S115: Yes), the image processing unit 91 ends this process. In contrast, when an instruction signal of instructing the ending is not input from the input unit 92 through the second control unit 94 (Step S115: No), the image processing unit 91 returns to Step S108 described above.

According to the first embodiment, since the difference detection unit 915 detects a difference between the simulation result of the blood flow flowing in the 3D model of the observation object acquired in advance and the analysis result of the blood flow flowing in the observation object and the output unit 916 outputs a difference result detected by the difference detection unit 915 to the display device 8, it is possible to compare the simulation result of the blood flow before surgery with the result of the blood flow during surgery in real time.

Further, according to the first embodiment, since the difference detection unit 915 detects a difference between the simulation image obtained by simulating the blood flow flowing in the 3D model acquired through the communication unit 95 and the blood flow analysis image generated by the blood flow analysis image generation unit 914 and the output unit 916 outputs any one or more of the simulation image, the difference image detected by the difference detection unit 915, the blood flow analysis image (the blood flow pattern), and the blood flow analysis result to the display device 8 based on the instruction signal input from the input unit 92 through the second control unit 94, it is possible to compare the simulation result of the blood flow before surgery with the result of the blood flow during surgery in real time.

Further, according to the first embodiment, since the blood flow analysis unit 913 analyzes the blood flow based on the 3D image data of which contrast is enhanced by the contrast image processing unit 911, it is possible to analyze the blood flow with high accuracy.

Further, according to the first embodiment, since the blood flow analysis unit 913 analyzes at least one or more of the blood flow speed, the blood flow rate, and the blood flow pattern, it is possible to obtain a plurality of kinds of analysis result desired by the operator.

Second Embodiment

Next, a second embodiment will be described. In the second embodiment, the other configurations are the same except that only the image processing unit 91 according to the first embodiment is different. For this reason, a configuration of the image processing unit according to the second embodiment will be described below. Additionally, the same reference numerals will be given to the same configurations as those of the medical observation system 1 according to the first embodiment and a detailed description thereof will be omitted.

Detailed Configuration of Image Processing Unit

Figure 17:
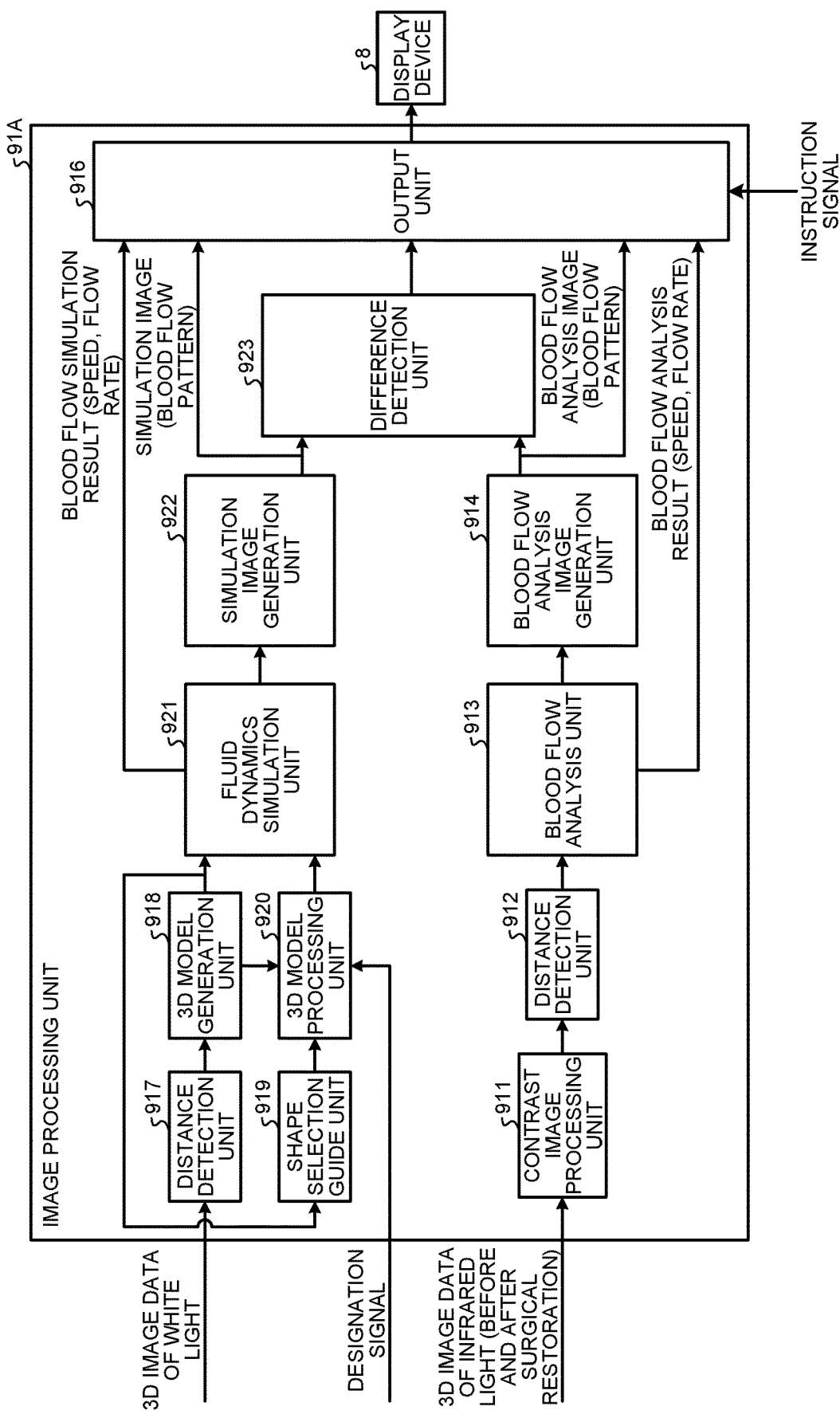
FIG. 17 is a block diagram illustrating a detailed configuration of an image processing unit according to a second embodiment.

FIG. 17 is a block diagram illustrating a detailed configuration of the image processing unit according to the second embodiment. An image processing unit 91A illustrated in FIG. 17 includes a distance detection unit 917, a 3D model generation unit 918, a shape selection guide unit 919, a 3D model processing unit 920, a fluid dynamics simulation unit 921, a simulation image generation unit 922, and a difference detection unit 923 in addition to the configuration of the image processing unit 91 according to the first embodiment. Additionally, in the second embodiment, the image processing unit 91A functions as a medical image processing device.

The distance detection unit 917 detects the distance information including a length in the vertical direction, a length in the horizontal direction, and a length in the depth direction of the observation object based on the 3D image data before surgical restoration and after surgical restoration due to white light input from the observation device 2.

The 3D model of the observation object (for example, aortic aneurysm) is generated based on the distance information calculated by the distance detection unit 917 and the 3D model generation unit 918. Additionally, the 3D model generation unit 918 may generate the 3D model of the organ of the subject to be treated based on a plurality of organ models (organ models such as heart, lung, and blood vessels) generated in advance and the distance information calculated by the distance detection unit 917.

The shape selection guide unit 919 outputs a plurality of replacement members applicable to the observation object to the display device 8 based on the distance information detected by the distance detection unit 917. Here, the plurality of replacement members are artificial blood vessels and stents having different thickness.

The 3D model processing unit 920 processes the 3D model in an arbitrary shape. The 3D model processing unit 920 generates the 3D model after surgical restoration by processing the 3D model based on a designation signal that designates any one of the plurality of replacement members input from the input unit 92 or the input unit 25.

The fluid dynamics simulation unit 921 simulates the blood flow flowing in the 3D model based on the 3D model before surgical restoration generated by the 3D model generation unit 918 or the 3D model after surgical restoration generated by the 3D model processing unit 920 using the known fluid dynamics.

The simulation image generation unit 922 generates a simulation image based on the 3D model before surgical restoration generated by the 3D model generation unit 918, the 3D model after surgical restoration generated by the 3D model processing unit 920, and the simulation result obtained by the simulation of the fluid dynamics simulation unit 921 and outputs the simulation image to the difference detection unit 923.

A difference result between the blood flow analysis image before and after surgical restoration and the simulation image obtained by simulating the blood flow flowing in the 3D model before and after surgical restoration generated by the difference detection unit 923 and the simulation image generation unit 922 is generated and each generated difference result is output to the output unit 916.

Process of Image Processing Unit

Figure 18:
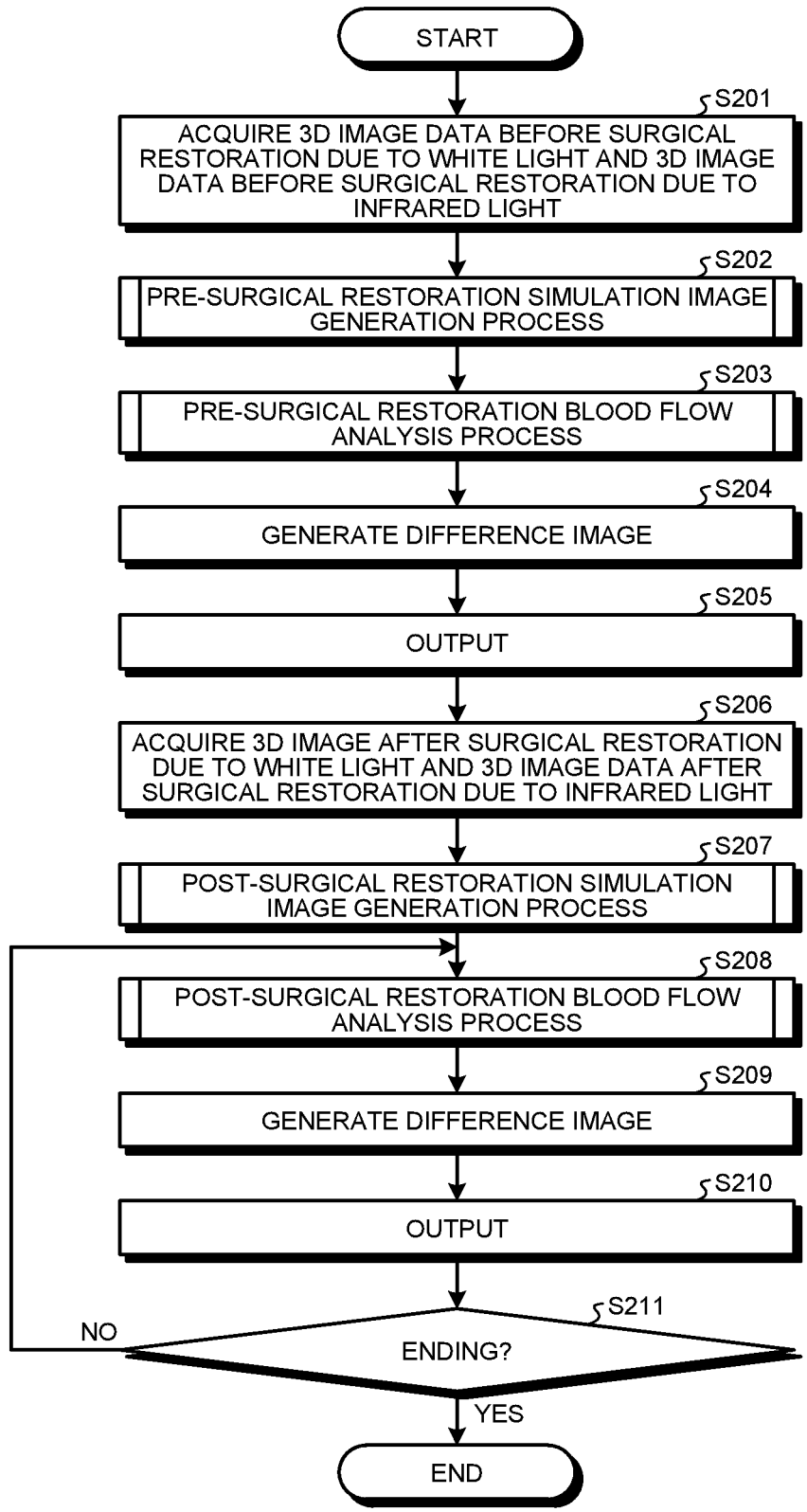
FIG. 18 is a flowchart illustrating an outline of a process performed by the image processing unit according to the second embodiment.

Next, a process which is executed by the image processing unit 91A will be described. FIG. 18 is a flowchart illustrating an outline of a process executed by the image processing unit 91A.

As illustrated in FIG. 18, the image processing unit 91A first acquires the 3D image data of white light and the 3D image data before surgical restoration due to infrared light from the observation device 2 (Step S201).

Subsequently, the image processing unit 91A performs a pre-surgical restoration simulation image generation process of generating the simulation image of the blood flow before surgical restoration based on the 3D image data of white light (Step S202). After Step S202, the image processing unit 91A proceeds to Step S203 to be described later.

Pre-Surgical Restoration Simulation Image Generation Process

Figure 19:
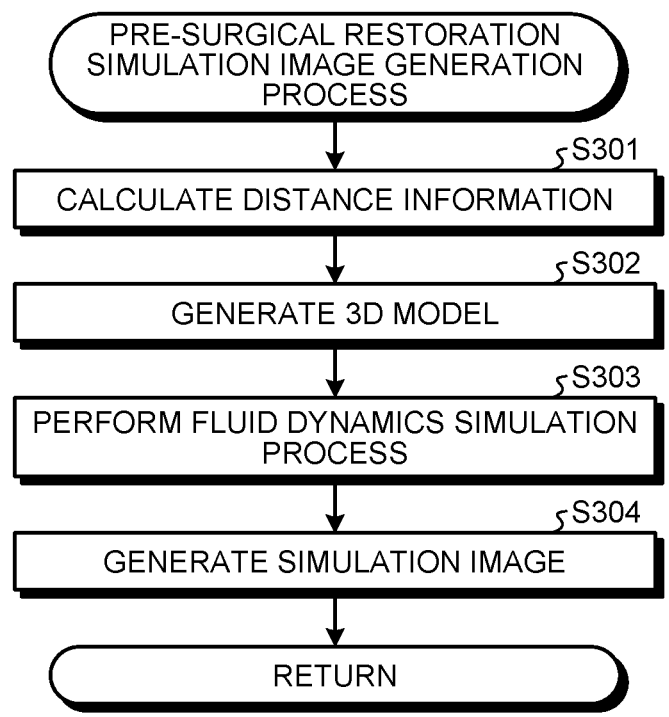
FIG. 19 is a flowchart illustrating an outline of a blood flow simulation image generation process of FIG. 18.

FIG. 19 is a flowchart illustrating an outline of the blood flow simulation image generation process of Step S202 of FIG. 18 described above.

As illustrated in FIG. 19, the distance detection unit 917 calculates the distance information including a length in the vertical direction, a length in the horizontal direction, and a length in the depth direction of the observation object based on the 3D image data before surgical restoration due to white light (Step S301).

Figure 20:
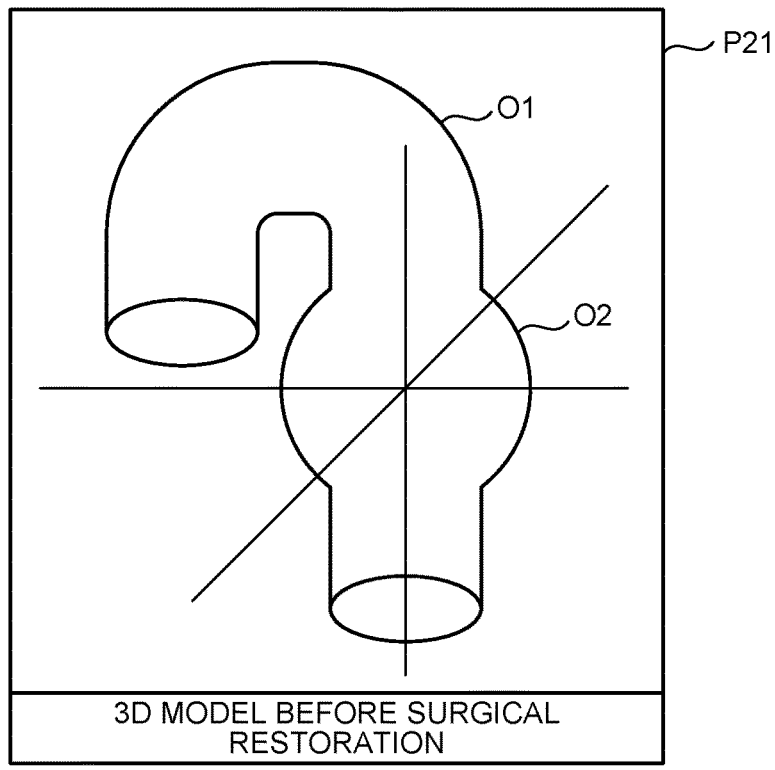
FIG. 20 is a diagram schematically illustrating a 3D model generated by a 3D model generation unit according to the second embodiment.

Subsequently, the 3D model generation unit 918 generates the 3D model of the observation object (for example, the aortic aneurysm) based on the distance information calculated by the distance detection unit 917 (Step S302). FIG. 20 is a diagram schematically illustrating the 3D model generated by the 3D model generation unit 918. As illustrated in FIG. 20, the 3D model generation unit 918 generates a 3D model image P21 before surgical restoration of the observation object (for example, the aortic aneurysm) based on the distance information calculated by the distance detection unit 917. The 3D model image P21 includes the aorta O1 and the aortic aneurysm O2.

Then, the fluid dynamics simulation unit 921 performs a fluid dynamics simulation process of the blood flow (the fluid) flowing in the 3D model generated by the 3D model generation unit 918 using the known fluid dynamics (Step S303).

Figure 21:
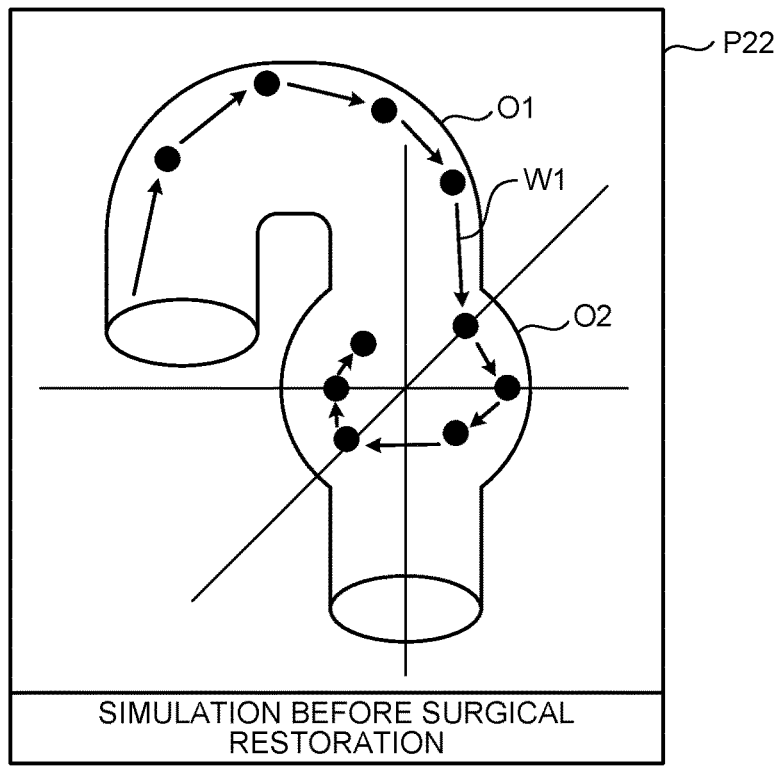
FIG. 21 is a diagram schematically illustrating a simulation image before surgical restoration.
Figure 22:
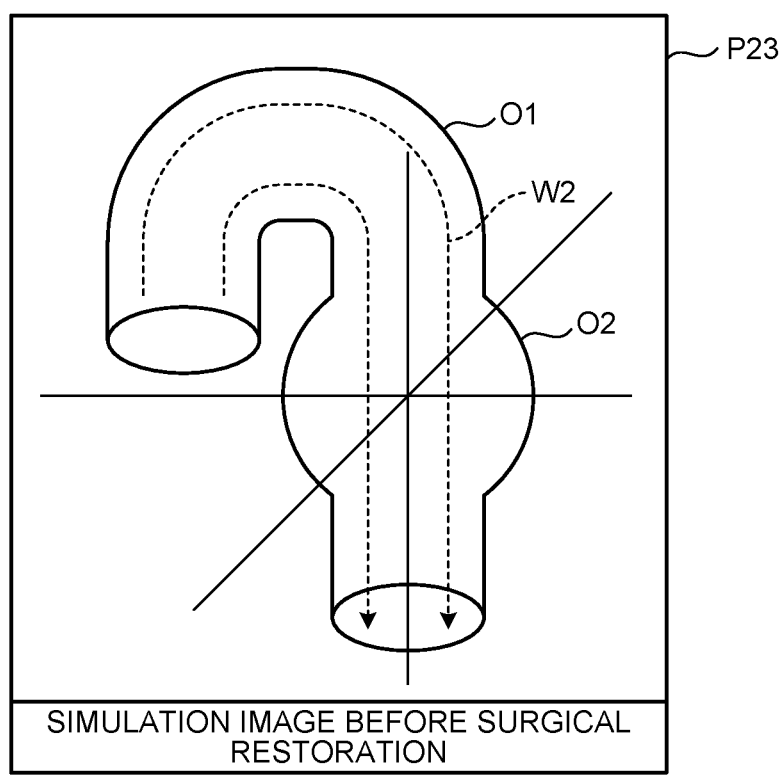
FIG. 22 is a diagram schematically illustrating a simulation image before surgical restoration.
Figure 23:
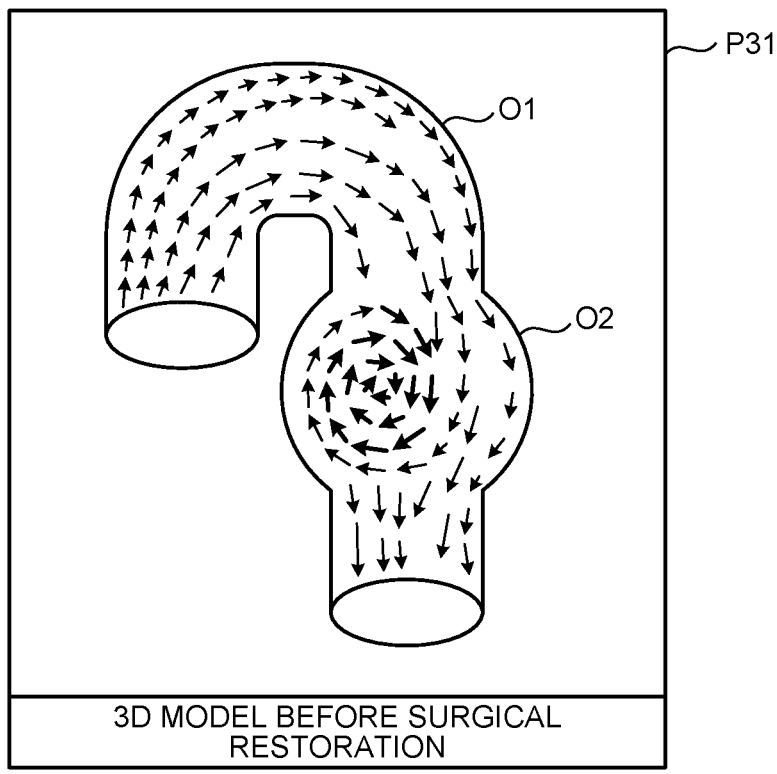
FIG. 23 is a diagram schematically illustrating another example of a simulation image before surgical restoration.
Figure 24:
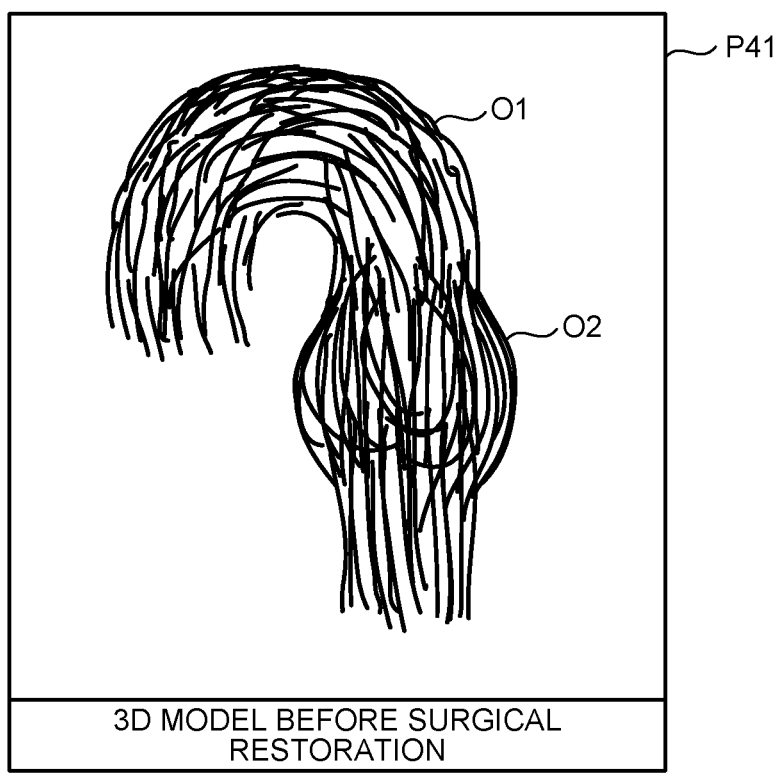
FIG. 24 is a diagram schematically illustrating another example of a simulation image before surgical restoration.

Subsequently, the simulation image generation unit 922 generates a simulation image based on the 3D model generated by the 3D model generation unit 918 and the simulation result obtained by the simulation of the fluid dynamics simulation unit 921 (Step S304). FIG. 21 is a diagram schematically illustrating the simulation image before surgical restoration. FIG. 22 is a diagram schematically illustrating the simulation image before surgical restoration. FIG. 23 is a diagram schematically illustrating another example of the simulation image before surgical restoration. FIG. 24 is a diagram schematically illustrating another example of the simulation image before surgical restoration. As illustrated in FIGS. 21 to 24, the simulation image generation unit 922 generates any one or more of the simulation images P21, P22, P31, and P41 based on the 3D model generated by the 3D model generation unit 918 and the simulation result obtained by the simulation of the fluid dynamics simulation unit 921. The simulation image P31 displays the direction of the blood flow, the flow rate of the blood flow, the speed of the blood flow, and the flow of the blood flow using arrows and colors based on the arrows. Further, the simulation image P41 displays the direction of the blood flow, the speed of the blood flow, and the flow of the blood flow in a linear shape and displays the speed and the flow rate of the blood flow by changing the colors of the lines to be identified. After Step S304, the image processing unit 91A returns to the main routine of FIG. 18.

Returning to FIG. 18, a description after Step S203 will be continued.

In Step S203, the image processing unit 91A performs a pre-surgical restoration blood flow analysis process of analyzing the blood flow in the simulation image based on the 3D image data before surgical restoration due to infrared light. After Step S203, the image processing unit 91A proceeds to Step S204 to be described later.

Pre-Surgical Restoration Blood Flow Analysis Process

Figure 25:
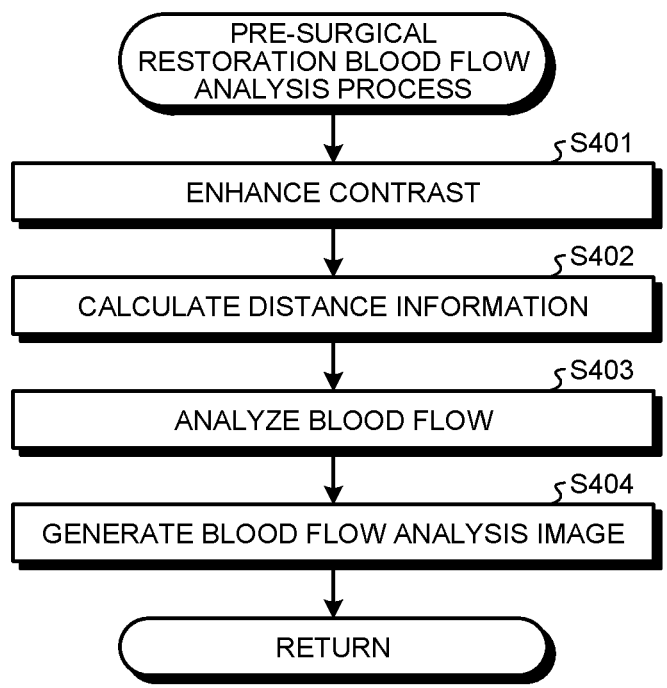
FIG. 25 is a flowchart illustrating an outline of a pre-surgical restoration blood flow analysis process of FIG. 18.

FIG. 25 is a flowchart illustrating an outline of the pre-surgical restoration blood flow analysis process of Step S203 of FIG. 18 described above.

As illustrated in FIG. 25, the contrast image processing unit 911 performs an image process of enhancing contrast on the 3D image data before surgical restoration due to infrared light and outputs the data to the distance detection unit 912 (Step S401).

Subsequently, the distance detection unit 912 calculates the distance information including a length in the vertical direction, a length in the horizontal direction, and a length in the depth direction of the observation object (the organ) based on the 3D image data having enhanced contrast before surgical restoration due to infrared light input from the contrast image processing unit 911 (Step S402).

Then, the blood flow analysis unit 913 analyzes the blood flow flowing in the 3D model (the organ) before surgical restoration based on the distance information calculated by the distance detection unit 912 (Step S403). Specifically, the blood flow analysis unit 913 analyzes the speed, diversion, and pattern of the blood flow flowing in the aorta O1 and the aortic aneurysm O2 of the 3D model before surgical restoration based on the 3D model image before surgical restoration generated by the 3D model generation unit 918 and the distance information detected by the distance detection unit 912.

Subsequently, the blood flow analysis image generation unit 914 generates the blood flow analysis image before surgical restoration based on the blood flow analysis result before surgical restoration analyzed by the blood flow analysis unit 913 (Step S404). Specifically, the infrared blood flow image P1, the blood flow analysis image P2, and the blood flow analysis image P3 illustrated in FIGS. 8 to 10 described above are generated. After Step S404, the image processing unit 91A returns to the main routine of FIG. 18.

Returning to FIG. 18, a description after Step S204 will be continued.

In Step S204, the difference detection unit 923 generates a difference image indicating a difference result between the blood flow analysis image and the simulation image obtained by the simulation of the blood flow flowing in the 3D model. Specifically, as illustrated in FIGS. 11 to 13, the difference detection unit 915 detects the regions R1 and R2 having a difference in the flow of the blood flow flowing in each of the simulation image P10 and the blood flow analysis image P11 and generates the difference image P12 in a state in which the regions R1 and R2 may be identified.

Subsequently, the output unit 916 outputs any one or more of the blood flow simulation result (the speed and the flow rate of the blood flow), the simulation image (the blood flow pattern), the difference image before surgical restoration detected by the difference detection unit 923, the blood flow analysis image (the blood flow pattern) before surgical restoration, and the blood flow analysis result before surgical restoration to the display device 8 based on the instruction signal input from the input unit 92 through the second control unit 94 (Step S205).

Subsequently, the image processing unit 91A acquires the 3D image data after surgical restoration due to white light and the 3D image data after surgical restoration due to infrared light from the observation device 2 (Step S206).

Then, the image processing unit 91A performs a post-surgical restoration simulation image generation process of generating the simulation image of the blood flow after surgical restoration based on the 3D image data after surgical restoration due to white light (Step S207). After Step S207, the image processing unit 91A proceeds to Step S208 to be described later.

Post-Surgical Restoration Simulation Image Generation Process

Figure 26:
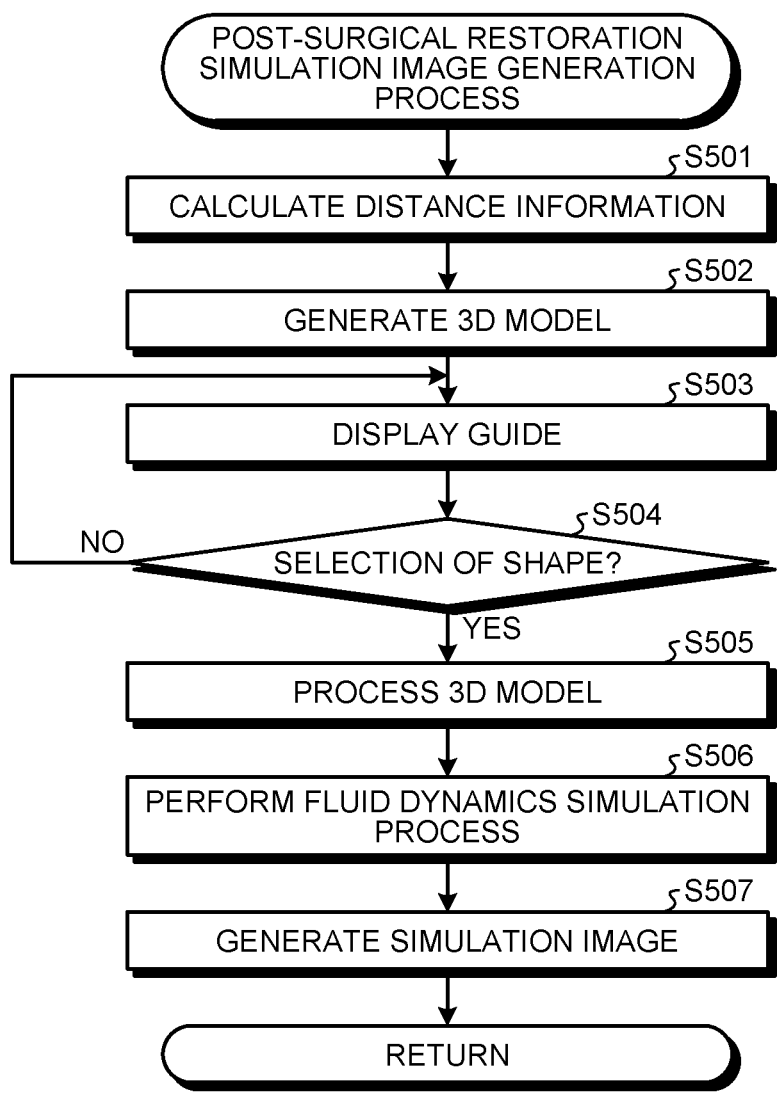
FIG. 26 is a flowchart illustrating an outline of a post-surgical restoration simulation image generation process of FIG. 18.

FIG. 26 is a flowchart illustrating an outline of the post-surgical restoration simulation image generation process of Step S207 of FIG. 18 described above.

As illustrated in FIG. 26, the distance detection unit 917 first calculates the distance information including a length in the vertical direction, a length in the horizontal direction, and a length in the depth direction of the observation object based on the 3D image data after surgical restoration due to white light (Step S501).

Subsequently, the 3D model generation unit 918 generates the 3D model of the observation object (for example, the aortic aneurysm) based on the distance information calculated by the distance detection unit 917 (Step S502).

Then, the shape selection guide unit 919 calculates the diameter of the blood vessel of the 3D model based on the distance information calculated by the distance detection unit 917 and the 3D model generated by the 3D model generation unit 918 and outputs and displays a plurality of artificial blood vessels based on the calculation result to the display device 8 (Step S503). The plurality of artificial blood vessels include a plurality of thicknesses and a plurality of shapes.

Subsequently, when a designation signal of designating any one of the plurality of artificial blood vessels displayed by the display device 8 is input from the input unit 92 through the second control unit 94 (Step S504: Yes), the image processing unit 91A proceeds to Step S505 to be described later. In contrast, when a designation signal of designating any one of the plurality of artificial blood vessels displayed by the display device 8 is not input from the input unit 92 through the second control unit 94 (Step S504: No), the image processing unit 91A returns to Step S503 described above.

Figure 27:
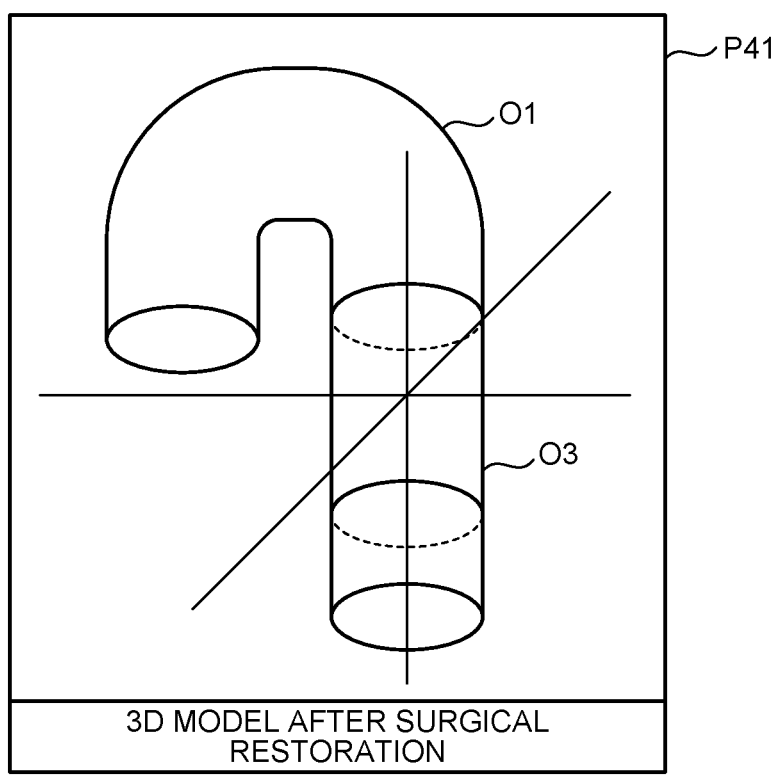
FIG. 27 is a diagram schematically illustrating a 3D model after surgical restoration generated by a 3D model processing unit according to the second embodiment.

In Step S505, the 3D model processing unit 920 generates a 3D model after surgical restoration processed by replacing an aortic aneurysm with an artificial blood vessel based on the 3D model and the artificial result designated by the designation signal input from the input unit 92 (Step S505). FIG. 27 is a diagram schematically illustrating the 3D model after surgical restoration generated by the 3D model processing unit 920. As illustrated in FIG. 27, the 3D model processing unit 920 generates a 3D model image P41 after surgical restoration processed by replacing an aortic aneurysm with an artificial blood vessel based on the 3D model and the artificial result designated by the designation signal input from the input unit 92. The 3D model image P41 includes the artificial blood vessel O3 that has replaced the aorta O1 and the aortic aneurysm O2.

Subsequently, the fluid dynamics simulation unit 921 performs a fluid dynamics simulation process of a blood flow (fluid) flowing in the 3D model after surgical restoration generated by the 3D model processing unit 920 using the known fluid dynamics (Step S506).

Figure 28:
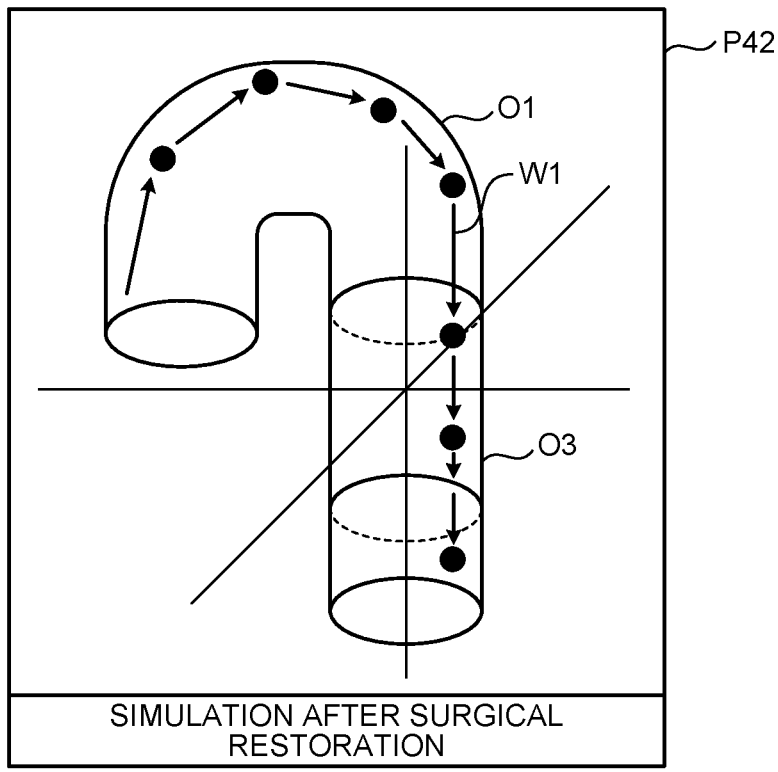
FIG. 28 is a diagram schematically illustrating a simulation image after surgical restoration.
Figure 29:
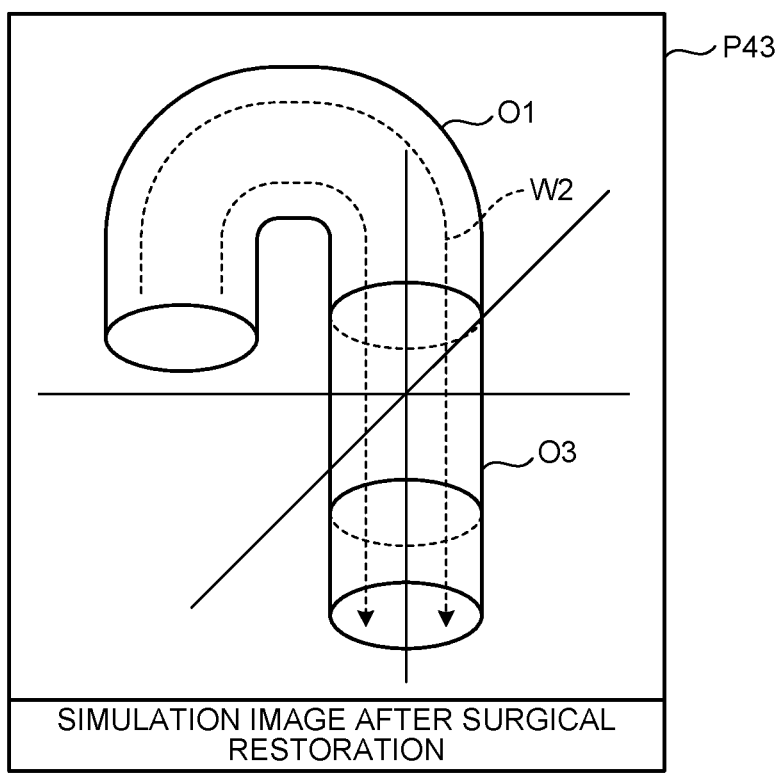
FIG. 29 is a diagram schematically illustrating a simulation image after surgical restoration.

Then, the simulation image generation unit 922 generates a simulation image after surgical restoration based on the 3D model after surgical restoration generated by the 3D model processing unit 920 and the simulation result obtained by the simulation of the fluid dynamics simulation unit 921 (Step S507). FIG. 28 is a diagram schematically illustrating the simulation image after surgical restoration. FIG. 29 is a diagram schematically illustrating the simulation image after surgical restoration. As illustrated in FIGS. 28 and 29, the simulation image generation unit 922 generates any one or more of simulation images P42 and P43 after surgical restoration based on the 3D model after surgical restoration generated by the 3D model processing unit 920 and the simulation result obtained by the simulation of the fluid dynamics simulation unit 921. After Step S504, the image processing unit 91A returns to the main routine of FIG. 18.

Returning to FIG. 18, a description after Step S208 will be continued.

In Step S208, the image processing unit 91A performs a post-surgical restoration blood flow analysis process of analyzing the blood flow flowing in the simulation image based on the 3D image data after surgical restoration due to infrared light. After Step S208, the image processing unit 91A proceeds to Step S209 to be described later.

Post-Surgical Restoration Blood Flow Analysis Process

FIG. 30 is a flowchart illustrating an outline of the post-surgical restoration blood flow analysis process of Step S203 of FIG. 18 described above.

As illustrated in FIG. 30, the contrast image processing unit 911 performs an image process of enhancing contrast on the 3D image data after surgical restoration due to infrared light and outputs the data to the distance detection unit 912 (Step S601).

Subsequently, the distance detection unit 912 calculates the distance information including a length in the vertical direction, a length in the horizontal direction, and a length in the depth direction of the observation object (the organ) based on the 3D image data having enhanced contrast after surgical restoration due to infrared light input from the contrast image processing unit 911 (Step S602).

Then, the blood flow analysis unit 913 analyzes the blood flow flowing in the 3D model (the organ) after surgical restoration based on the distance information calculated by the distance detection unit 912 (Step S603). Specifically, the blood flow analysis unit 913 analyzes the speed, diversion, and pattern of the blood flow flowing in the aorta O1 and the artificial blood vessel O3 of the 3D model after surgical restoration based on the 3D model image after surgical restoration generated by the 3D model generation unit 918 and the distance information detected by the distance detection unit 912.

Subsequently, the blood flow analysis image generation unit 914 generates the blood flow analysis image after surgical restoration based on the blood flow analysis result after surgical restoration analyzed by the blood flow analysis unit 913 (Step S604). Specifically, the infrared blood flow image P4, the blood flow analysis image P5, and the blood flow analysis image P6 illustrated in FIGS. 14 to 16 described above are generated. After Step S604, the image processing unit 91A returns to the main routine of FIG. 18.

Returning to FIG. 18, a description after Step S209 will be continued.

In Step S209, the difference detection unit 923 generates a difference image indicating a difference result between the simulation image after surgical restoration obtained by simulating the blood flow flowing in the 3D model and the blood flow analysis image after surgical restoration.

Subsequently, the output unit 916 outputs any one or more of the blood flow simulation result (the blood flow speed and the flow rate) after surgical restoration, the simulation image (the blood flow pattern) after surgical restoration, the difference image after surgical restoration detected by the difference detection unit 923, the blood flow analysis image (the blood flow pattern) after surgical restoration, and the blood flow analysis result after surgical restoration to the display device 8 based on the instruction signal input from the input unit 92 through the second control unit 94 (Step S210).

Then, when an instruction signal of instructing the ending is input from the input unit 92 through the second control unit 94 (Step S211: Yes), the image processing unit 91A ends this process. In contrast, when an instruction signal of instructing the ending is not input from the input unit 92 through the second control unit 94 (Step S211: No), the image processing unit 91 returns to Step S208 described above.

According to the second embodiment, since the difference detection unit 923 detects a difference between the simulation image generated by the simulation image generation unit 922 and the blood flow analysis image generated by the blood flow analysis image generation unit 914 and the output unit 916 outputs any one or more of the blood flow simulation result (the speed and the flow rate of the blood flow) before and after surgical restoration, the simulation image (the blood flow pattern) before and after surgical restoration, the difference image before and after surgical restoration detected by the difference detection unit 923, the blood flow analysis image (the blood flow pattern) before and after surgical restoration, and the blood flow analysis result before and after surgical restoration to the display device 8 based on the instruction signal input from the input unit 92 through the second control unit 94, it is possible to compare the simulation result of the blood flow before surgery with the result of the blood flow during surgery in real time.

Further, according to the second embodiment, since the fluid dynamics simulation unit 921 simulates the blood flow flowing in the 3D model processed into an arbitrary shape by the 3D model processing unit 920, it is possible to compare the actual blood flow simulation result after surgical restoration with the blood flow result before surgical restoration in real time.

Further, according to the second embodiment, since the shape selection guide unit 919 outputs a plurality of replacement members applicable to the observation object to the display device 8 based on the distance information detected by the distance detection unit 917 and the 3D model processing unit 920 generates the 3D model after surgical restoration by processing the 3D model based on the designation signal of designating any one of the plurality of replacement members, it is possible to select the replacement member after surgical restoration suitable for the observation object by an intuitive operation and to improve the efficiency of the treatment.

Additionally, in the second embodiment, the 3D model generation unit 918 generates only the front 3D model, but the present disclosure is not limited thereto. For example, the CT image data or the MIR image data stored in the external server described in the first embodiment may be combined to generate the rear 3D model. Accordingly, it is possible to more accurately simulate the blood flow before and after surgical restoration.

Other Embodiments

Additionally, in the first and second embodiments of the present disclosure, the observation device 2 capable of generating the 3D image data has been described as an example, but the present disclosure may be also applied to, for example, an endoscope capable of generating 3D image data.

Further, in the first and second embodiments of the present disclosure, the image processing units 91 and 91A output any one or more of the blood flow simulation result (the blood flow speed and the flow rate) after surgical restoration, the simulation image (the blood flow pattern) after surgical restoration, the difference image after surgical restoration detected by the difference detection unit 923, the blood flow analysis image (the blood flow pattern) after surgical restoration, and the blood flow analysis result after surgical restoration to the display device 8. However, for example, the image processing units 91 and 91A may be provided with a display monitor having a display function. Of course, when the display monitor and the image processing units 91 and 91A are provided, the present disclosure may be also applied to a portable terminal device or portable device.

Further, variations may be formed by appropriately combining a plurality of components disclosed in the medical observation systems according to the first and second embodiments of the present disclosure. For example, some components may be deleted from all the components described in the medical observation systems according to the first and second embodiments of the present disclosure. Further, the components described in the medical observation systems according to the first and second embodiments of the present disclosure may be appropriately combined.

Further, in the medical observation systems according to the first and second embodiments of the present disclosure, the "part" described above may be read as "means" or "circuit". For example, the control unit may be read as a control unit or a control circuit.

Further, a program to be executed in the medical observation system according to the first and second embodiments of the present disclosure is provided as a computer-readable recording medium such as a CD-ROM, a flexible disk (FD), a CD-R, a Digital Versatile Disk (DVD), a USB medium, and a flash memory as file data in an installable or executable format.

Further, a program to be executed in the medical observation systems according to the first and second embodiments of the present disclosure may be stored in a computer connected to a network such as an internet and may be downloaded through a network to be provided.

Additionally, in the description of the timing chart in this specification, the order of the process between the timings is specified using expressions such as "first", "after", and "continue", but the order of processes necessary to implement the present disclosure is not uniquely defined by those expressions. That is, the order of the processes in the timing chart described in this specification may be changed within a consistent range.

According to the present disclosure, there is an effect that a simulation result of a blood flow before surgery and a result of a blood flow during surgery may be compared with each other in real time.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising circuitry configured to:
   analyze a blood flow flowing in an observation object based on a medical observation image obtained by capturing an image of the observation object;
   obtain distance information of the observation object; and
   generate, based on the distance information, a difference result between a simulation result of a blood flow flowing in a 3D model acquired in advance for the observation object and an analysis result of a blood flow flowing in the observation object.

2. The medical image processing device according to claim 1, wherein
   the distance information includes a length in a vertical direction, a length in a horizontal direction, and a length in a depth direction of the observation object, the distance information being detected based on 3D image data having a parallax input from the outside and generated by receiving each of two subject images respectively formed by a pair of left and right optical systems when the observation object including at least an organ is irradiated with at least infrared light,
   the medical observation image is the 3D image data, and
   the circuitry is configured to analyze each blood flow before and after surgical restoration flowing in the observation object based on two 3D image data generated when infrared light is irradiated before and after surgical restoration of the observation object based on the detected distance information.

3. The medical image processing device according to claim 2, wherein the circuitry is configured to
   generate each blood flow analysis image before and after surgical restoration based on each blood flow analysis result before and after surgical restoration in the analyzed observation object, and
   generate a difference result between a simulation image of a blood flow flowing in a 3D model acquired in advance for the observation object and each blood flow analysis image before and after surgical restoration.

4. The medical image processing device according to claim 3, wherein the circuitry is configured to output the detected difference result to a display, the circuitry being configured to select and output, to the display based on an input instruction signal, any one or more of:
   each detected difference result before and after surgical restoration, each blood flow analysis result before and after surgical restoration flowing in the observation object,
   each blood flow analysis image before and after surgical restoration, and
   the simulation image.

5. The medical image processing device according to claim 4, wherein the circuitry is configured to
   perform an image process of enhancing contrast on two 3D image data generated when infrared light is irradiated before and after surgical restoration of the observation object, and
   analyze each blood flow before and after surgical restoration flowing in the observation object based on the two 3D image data of which contrast is enhanced.

6. The medical image processing device according to claim 3, wherein the circuitry is configured to analyze any one or more of a speed, a flow rate, and a pattern of the blood flow.

7. The medical image processing device according to claim 3, wherein the circuitry is configured to:
   generate a 3D model of the observation object based on the distance information;
   simulate a blood flow flowing in the 3D model based on the 3D model;
   generate the simulation image based on the generated 3D model and the obtained simulation result; and
   generate a difference result between the generated simulation image and each blood flow analysis image before and after surgical restoration.

8. The medical image processing device according to claim 7, wherein the circuitry is configured to:
   process the 3D model into an arbitrary shape; and
   simulate a blood flow flowing in the 3D model processed into the arbitrary shape.

9. The medical image processing device according to claim 8, wherein the circuitry is configured to:
   output a plurality of replacement members applicable to the observation object to a display based on the distance information; and
   generate a 3D model after surgical restoration by processing the 3D model based on a designation signal that designates any one of the plurality of replacement members.

10. A medical observation system comprising:
    the medical image processing device according to claim 1; and
    an observation device including: an imager configured to receive each of two subject images respectively formed by a pair of left; and right optical systems, the observation device being configured to irradiate the observation object with infrared light and generate the medical observation image by receiving reflected light reflected by the observation object and light emitted from the observation object using the imager.

11. An image processing method comprising:

analyzing, using circuitry, a blood flow flowing in an observation object based on a medical observation image obtained by capturing an image of the observation object;

obtaining, using the circuitry, distance information of the observation object;

calculating, using the circuitry, based on the distance information, a difference between a simulation result of a blood flow flowing in a 3D model acquired in advance for the observation object and an analysis result of a blood flow flowing in the observation object; and generating, using the circuitry, a difference result between the simulation result and the analysis result of the blood flow flowing in the observation object.

12. A non-transitory computer readable medium including executable instructions, which when executed by a computer cause the computer to execute an image processing method, the method comprising:

analyzing a blood flow flowing in an observation object based on a medical observation image obtained by capturing an image of the observation object;

obtaining distance information of the observation object;

calculating, based on the distance information, a difference between a simulation result of a blood flow flowing in a 3D model acquired in advance for the observation object and an analysis result of a blood flow flowing in the observation object; and generating a difference result between the simulation result and the analysis result of the blood flow flowing in the observation object.

13. The medical image processing device according to claim 1, wherein the distance information includes a length in a vertical direction, a length in a horizontal direction, and a length in a depth direction of the observation object.

* * * * *